United States Patent [19]
Schmitz

[11] Patent Number: 5,693,165
[45] Date of Patent: Dec. 2, 1997

[54] METHOD AND APPARATUS FOR MANUFACTURING AN ABSORBENT ARTICLE

[75] Inventor: Christoph Schmitz, Euskirchen-Stotzheim, Germany

[73] Assignee: The Procter & Gamble Company, Cincinnati, Ohio

[21] Appl. No.: 633,741

[22] PCT Filed: Oct. 26, 1994

[86] PCT No.: PCT/US94/12286

§ 371 Date: Apr. 19, 1996

§ 102(e) Date: Apr. 19, 1996

[87] PCT Pub. No.: WO95/12491

PCT Pub. Date: May 11, 1995

[30] Foreign Application Priority Data

Nov. 4, 1993 [EP] European Pat. Off. ............ 93117893

[51] Int. Cl.[6] .................................................. A61F 13/15
[52] U.S. Cl. .................. 156/164; 156/163; 156/229; 156/494; 156/495; 156/496; 604/385.2
[58] Field of Search .......................... 156/164, 163, 156/160, 229, 494–496; 226/96, 124, 158; 604/385.2

[56] References Cited

U.S. PATENT DOCUMENTS

| | | | |
|---|---|---|---|
| 4,236,955 | 12/1980 | Prittie | 156/353 |
| 4,987,940 | 1/1991 | Straub et al. | 156/164 |
| 5,109,767 | 5/1992 | Nyfeler et al. | 101/23 |
| 5,127,981 | 7/1992 | Straub et al. | 156/496 X |

FOREIGN PATENT DOCUMENTS 2370589  6/1978  France .

*Primary Examiner*—Jeff H. Aftergut
*Attorney, Agent, or Firm*—Kevin C. Johnson; Steven W. Miller; Jacobus C. Rasser

[57] ABSTRACT

The invention relates to a method of manufacturing an absorbent article (144), wherein the speed of a part (7b) of a continuously moving web (1) comprising a topsheet (121), backsheet (123), core (120) or any combination thereof, is periodically varied, while maintaining a constant speed of the upstream (3) and downstream (5) parts of the web (1). The method comprises feeding the web (1) past rotating transportation rollers (13, 15) which are oscillated parallel to the web (1) in the direction of transportation (F) and opposite to the direction of transportation (F). Three web sections (7a, 7b, 7c) are during oscillation of the transportation rollers (13, 15) maintained in a mutually parallel relationship. Translation means (77) and rotation balancing means (63, 63') allow the transportation rollers (13, 15) to be driven at high speeds and low variations in torque. The strain exerted on the web (1) remains relatively low and is limited to the inertia forces that act on the web (1).

20 Claims, 14 Drawing Sheets

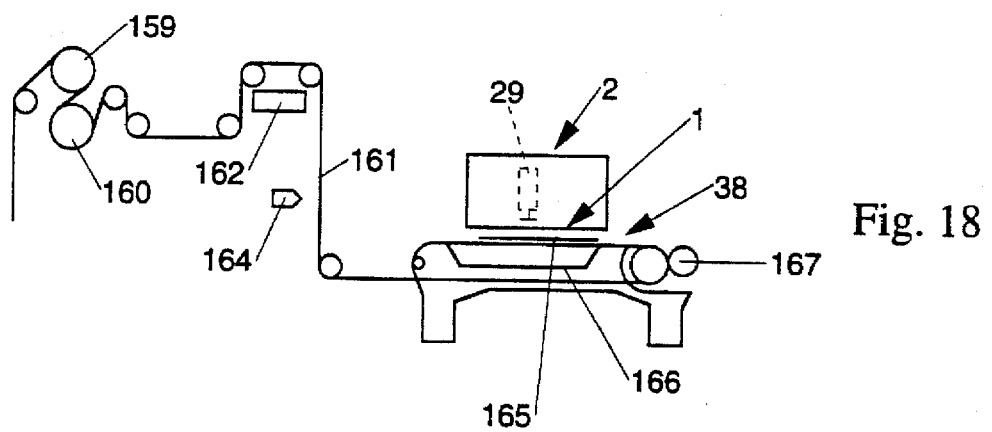
Fig. 18
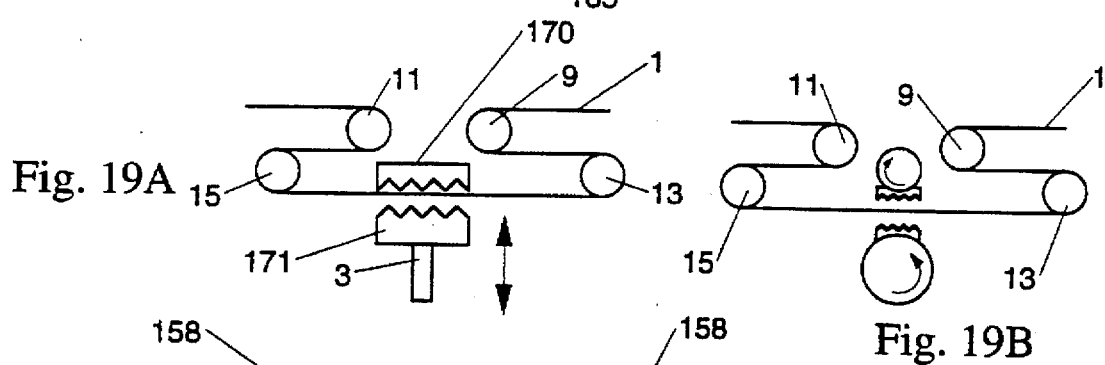
Fig. 19A
Fig. 19B
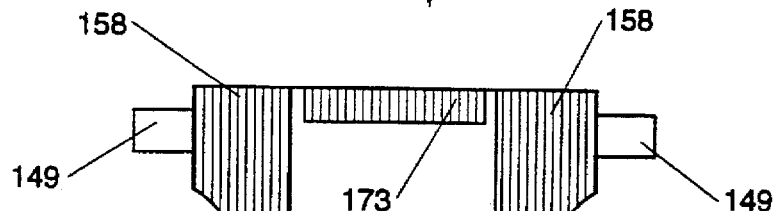
Fig. 20
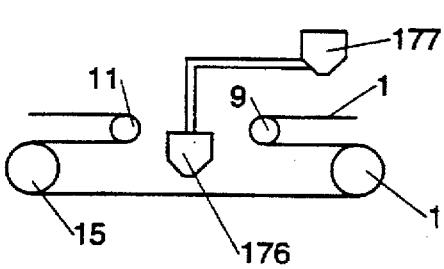
Fig. 21

METHOD AND APPARATUS FOR MANUFACTURING AN ABSORBENT ARTICLE

FIELD OF THE INVENTION

The invention relates to a method of making an absorbent article comprising a liquid pervious topsheet, a liquid-impervious backsheet and an absorbent core interposed between the topsheet and the backsheet, the method comprising the steps of:

a feeding a web, comprising the topsheet, the backsheet or the core or a combination thereof along a stationary frame, along an upstream trajectory, a downstream trajectory, and an intermediate trajectory comprised between the upstream trajectory and the downstream trajectory, the web having along the upstream trajectory and along the downstream trajectory a substantially constant speed of transport, the upstream and the downstream trajectory being substantially stationary relative to the frame, b running the web along an upstream and a downstream transport roller that are periodically displaceable, and c periodically displacing the transport rollers around a stationary equilibrium position.

The invention also relates to an apparatus for carrying out the method according to the invention.

BACKGROUND OF THE INVENTION

It is well known in the art to produce absorbent articles such as disposable diapers by combining a liquid pervious topsheet, a liquid impervious backsheet and an absorbent core to form a continuously moving web. In the American patent U.S. Pat. No. 4,081,301, a method is described to continuously attach discrete lengths of elastic ribbon to the moving web by feeding a continuous elastic ribbon in a pre-stretched state into the nip in which the topsheet and backsheet are joined around the absorbent core. The continuous elastic ribbon which runs along the longitudinal sides of the web, is provided with adhesive at pre-determined intervals. After cutting the web transversely to form individual diapers, parts of the elastic ribbons that have not been provided with glue, retract to their relaxed state to be positioned within the periphery of the topsheet and the backsheet, without gathering the topsheet and the backsheet in the unattached areas.

From the European Patent EP-A-0 256 869 it is known to pass a continuous fibrous web having multiple corrugations, under a powder depositing orifice to deposit an absorbent powder, such as a water-swellable polymeric material in the corrugations. After passing under the powder depositing orifice, the web is fed to a motion changing device to change the movement of the web from continuous to intermittent motion. The motion changing device comprises a vertically oscillating roller, under which the web is passed. When the roller travels downwardly, the web at the upstream side of the roller is stored along the extra path length created by the downward movement, the motion of the web downstream of the roller being stopped.

The above method has as a disadvantage that all the web downstream of the oscillating roller is accelerated and decelerated by the reciprocation of the vertical roller. The interruption of movement of the web may interfere with the functioning of applicator devices located downstream of the vertical roller. Also the accelerations acting on the web by changing the speed of all of the web downstream of the vertical roller, results in a relatively high strain being exerted on the web.

From U.S. Pat. No. 4,399,905 an apparatus for forming a stack of articles is known, in which a flight of grippers are mounted on an endless belt. The belt is looped around transport members, which are reciprocated so that a part of the belt is cyclically stopped, at a continuous drive of the belt. By moving the transport members against the direction of transport of the belt, with the transport velocity, the speed of the belt relative to stationary frame of the stacker is stopped.

A disadvantage of the above apparatus is that the velocity of the reciprocating transport member needs to equal the speed of transport of the belt for a part of the belt to become stationary. Furthermore, the path length of the part of the belt that extends between the transport member and a stationary roller, changes upon reciprocation of the transport member. Hence, the known apparatus can only be used in combination with a chain or a toothed belt but not in combination with a flat web or relatively low strength.

The European Patent Application EP-A-0 364 087 discloses an applicator device for applying layers of material generally transversely across an elongated web. The elongated web moves continuously through the device in the machine direction at a predetermined web speed. The machine direction corresponds to the longitudinal direction of the web. The device comprises two transport members which each deflect the web through 90°, in the plane of the web. A transverse web portion of constant length, extending perpendicular to the machine direction, is comprised between the transport members, which are formed by air bars. The transport members are mounted on a can which can be reciprocated in the machine direction.

When the transport members are moved in the transport direction of the web, at a speed which equals the web speed, the web portion between the transport members is stationary relative to the transport members. The transverse web portion is in this case stationary in the direction perpendicular to the machine direction, i.e. in the cross machine direction. A rotating applicator wheel, having a tangential speed which equals the linear speed of the air bars, can contact the transverse web portion to attach a layer of material. Upon reversal of the movement of the air bars against the web's feed direction, the transverse web portion is accelerated past the air bars to the web's downstream side. The device can be used to apply layers of liquid such as ink, paint or adhesive or layers of film, paper, nonwovens or tape to webs. The device was found particularly suitable for applying elastic material, reinforcing layers, fasteners, moisture barriers etc. to a polymeric web adapted to subsequently be cut during the manufacture of disposable garments such as diapers.

Although the above device is effective in changing the speed of only a pre-determined portion of a web, the upstream and downstream parts being run at constant speed, the device introduces to the web portion a net speed component which is parallel to the direction of transport of the web. An applicator device is therefore necessary that moves with the speed of displacement of the air bars parallel to the transport direction, for the application of the transverse features to the web.

For completely stopping of the movement of the web relative to the transport members, the transport members need to travel with speed of transport, opposite to the incoming web. Especially at high web speeds, the transport members will be subject to large accelerations.

Another disadvantage of the known device, is that the centre line of the downstream part of the web is displaced in the cross-machine direction, with respect the centre line of the upstream part of the web.

Furthermore, the above apparatus introduces significant stress to the web as it is pulled over two non-rotating bars such that friction forces are exerted which are proportional to the exponential value of the coefficient of friction.

From the European Patent application EP-A-0 284 652 it is known to supply tensioned elastic ribbons transversely to a continuously moving web at a high speed. A number of applicator heads are mounted on a rotatable vertical shaft, each applicator head being connected to a radial arm. Upon rotation of the shaft, the arms pass over the moving web. At the position when a radial arm extends perpendicular to the web and has a tangential velocity equal to the linear web speed, a pre-stretched elastic is fed from the applicator head. A rotating anvil, which has a circumferential velocity equal to the linear web speed to minimise the shearing forces, contacts the applicator head upon attachment of the elastic.

The above apparatus can, because of its multiple arms, attach transverse parts to the moving web at high speed and exerts a low tension on the web. However, the speed of the whole web is constant. For application of transverse parts to a web that require for instance, due to their complexity, momentarily stopping the web at the position of the applicator device, the above apparatus is less suitable.

It is an object of the invention to provide a method of manufacturing an absorbent article whereby the speed of the web can be varied while keeping the speed of the main upstream and downstream parts of the web constant.

It is another object of the invention to periodically vary the speed of a part of the web at high frequencies and high web speeds while keeping the speed of the main-upstream and downstream parts of the web constant.

It is again another object of the invention to vary the speed of a part of the web exerting a low variation in tension on the web.

It is a further object of the invention to vary the speed of a part of the web without introducing significant frictional forces on the web.

It is a further object of the invention to vary the speed of a part of the web without causing movement of said part in a direction transverse to the direction of transport of the web.

SUMMARY OF THE INVENTION

The method according to the invention comprises running the web along an upstream and downstream guide roller, which rollers are translationally stationary relative to the frame and along an upstream and downstream transport roller that are periodically displaceable.

A first section of the intermediate trajectory of the web extends between the upstream guide roller and the upstream transport roller.

A second, constant-length, section of the intermediate trajectory extends between the upstream and downstream guide rollers or between the upstream and downstream transport rollers. When the second section extends between the upstream and the downstream guide rollers, the section is stationary relative to the frame. When the second section of the intermediate trajectory extends between the upstream and the downstream transport roller, the section is translated relative to the frame.

A third section of the intermediate trajectory extends between the downstream guide roller and the downstream transport roller. The first and third sections of the intermediate trajectory are parallel to the second section of the intermediate trajectory.

When the transport rollers are reciprocated in a direction parallel to the second section of the intermediate trajectory, the lengths of the first and third sections of the intermediate trajectory are varied, while keeping constant the total length of the intermediate trajectory and while keeping constant the length of the second section of the intermediate trajectory.

The transport rollers are rotated such that the strain exerted on the web in running the web past the transport rollers is not substantially larger than the strain exerted on the web by the inertia forces acting on the web.

Because of the constant length of the intermediate trajectory of the web, the time it takes for a part of the web to travel along the length of the intermediate trajectory is constant and is independent of the location of the intermediate trajectory relative to the stationary frame. Hence, the movement of those parts of the web that are located along the upstream and downstream trajectories, is not affected by the direction and the speed of the displacement of the intermediate trajectory relative to the frame.

Therefore, by moving the intermediate trajectory of the web relative to the stationary frame, the speed at which the web travels along the intermediate trajectory can be adapted such that for those parts of the web that are located along the intermediate trajectory, the velocity relative to the stationary frame is increased, reduced, or reversed.

As the transport rollers are cyclically moved relative to the frame, the rate at which the web travels along the transport rollers varies around the constant speed of transport of the web along the upstream and the downstream trajectories. The amplitude of the cyclical velocity of the web along the transport rollers equals the amplitude of the velocity with which the transport rollers are reciprocated relative to the frame. Hence, by driving the transport rollers in synchronism with the displacement of the transport rollers, the acceleration and deceleration forces for modulating the speed of the transport rollers are passed to the transport rollers by the drive means, instead of by the web. This allows relatively weak webs to be accelerated and decelerated by the method according to the invention, a low strain being exerted on the webs.

Relative to the stationary frame, the second section of the intermediate trajectory can be stationary or can be translationally displaced.

When the second section of the intermediate trajectory extends between a stationary upstream and a stationary downstream guide roller, the second section is stationary relative to the frame. An embodiment of the method according to the invention, in which the second section of the intermediate trajectory is stationary, is arrived at by passing the web along a path formed by an upper and a lower S-shaped loop. The bottom leg of the upper S-shaped loop is connected to the top leg of the lower S-shaped loop. The first and third sections of the intermediate trajectory correspond to the middle legs of the upper S-shaped loop and the lower S-shaped loop respectively. The second section of the intermediate trajectory corresponds to the combined bottom leg of the upper S-shaped loop and the top leg of the lower S-shaped loop.

Two stationary guide rollers are located in the bottom half of the upper S-shaped loop and the top half of the lower S-shaped loop respectively. Two transport rollers are located in the top half of the upper S-shaped loop and the bottom half of the lower S-shaped loop respectively.

The incoming web is fed from the upstream trajectory, past the upstream transport roller to the upstream guide roller, continues past the downstream guide roller to the downstream transport roller to the downstream trajectory. By moving the transport rollers in the transport direction of the incoming web at half the web speed, the incoming web is stored along the increased length of the top half of the upper S-shaped loop. The parts of the web that are located along the second section of the intermediate trajectory are then stationary relative to the frame.

By moving the transport rollers against the transport direction, the length of web that was stored along the top half of the upper S-shaped loop is accelerated along the second section of the intermediate trajectory, and is fed to the downstream trajectory of the web.

The first embodiment in which the second section of the intermediate trajectory is periodically translated relative to the stationary frame can be arrived at by interchanging the positions of the transport rollers and the guide rollers in the previously described upper and lower S-shaped loop configuration. In this case, when the transport rollers are moved against the direction of transport of the incoming web at half the web speed, part of the incoming web is stored along the first trajectory, and part of the incoming web travels along the second trajectory at half the web speed, in the transport direction of the web. As the second section of the intermediate trajectory itself moves against the transport direction of the web, the position of the web relative to the frame is again stationary.

A preferred embodiment of the method according to the invention, in which the second section of the intermediate trajectory is translated, comprises feeding the web in a configuration which is formed by a first S-shape loop and a reverse S-shaped loop, which are connected in a back-to-back manner via their lower legs. The transport rollers are located in the lower halves of each S-shaped loop and the guide rollers are located in the top halves of each S-shaped loop.

The first and third sections of the intermediate trajectory correspond to the middle legs of both S-shaped loops and the second section of the intermediate trajectory corresponds to the combined lower legs of the S-shaped loops. The advantage of the above configuration, is that the upstream and the downstream trajectories of the web are located in the same plane and that the centre line of the downstream trajectory is not displaced.

It is essential in the method according to the invention, that the first and third sections of the intermediate trajectory are parallel to the third section. The term "parallel" is intended to include curvilinear trajectories, the perpendicular distance between which is constant. For instance, all sections of the intermediate trajectory may be located along straight lines, or the first and third sections of the intermediate trajectory may be located on segments of a first circle, the second section being located on a segment of a second circle, which is concentric with the first circle. Only when the parallel relationship between the first and third sections on the one hand, and the second section on the other hand, is maintained, will the total length of the intermediate trajectory be constant, independent of the position of the transport rollers.

By periodically varying the speed of the transport rollers with an amplitude of half the speed of transport of the web, the speed of the web relative to the frame periodically becomes zero, in three perpendicular directions. This allows operations to be performed on the web by applicator apparatus interacting with the web, the applicator apparatus being positionally stationary relative to the frame.

As the maximum speed of the transport rollers can be limited to half the web speed or less, in order to temporarily stop the web, the method can be applied at high frequencies and high web speeds, while maintaining the accelerations of the transport rollers relatively small.

In the method according to the invention, the centre lines of the upstream and the downstream parts of the web are not displaced in a direction parallel to the plane of the web. This allows the method to be used in production lines through which the web passes in a straight line, without having to realign the downstream part of the production line, or the use of an extra deflection member to realign the centre liner of the downstream part of the web.

In an embodiment of the method according to the invention, also the guide rollers are rotated to reduce the strain exerted on the web by the guide rollers. The guide rollers can be driven at a constant speed, such that their circumferential velocity corresponds to the transport velocity, $V_0$, of the web.

Because of the low strain exerted on the web by the transport rollers and the guide rollers, the web can be passed along the rollers at the high speeds, such as 5 m/s, and higher which are customary in disposable diaper manufacture.

In one embodiment of the method and apparatus according to the invention, the guide rollers and the transport rollers are driven by a drive member which is coupled with the guide rollers and the transport rollers to form a closed loop, a part of which extends parallel to the intermediate trajectory, the drive member being driven at a constant speed, which equals the speed of transport of the web.

Running a drive belt in parallel with the web, allows the guide rollers to be driven at a constant speed and the transport rollers to be driven at a cyclically varying speed, by a single constant speed drive motor. The torque for driving the rollers is derived from the drive belt, rather than from the web, so that the relatively weak webs used in diaper manufacture can be run through the apparatus.

A further embodiment of the apparatus in accordance with the invention comprises rotation-balancing means which are rotationally coupled to the transport rollers, the rotation-balancing means being comprised of a two discs which are rotationally mounted on the frame. Each disc is linked to a pair of pulleys by a belt. The pulleys are connected to the sled on which the transport rollers are mounted, one pulley of each pair being driven by a respective transport member. A belt forms a closed loop around each disc and the respective pulleys. When the sled is reciprocated, the pulleys are translated within each closed loop of the balancing means, so that the speed of rotation of each disc differs in phase from the speed of rotation of the transport members by 180°, i.e. the speed of the discs increases when the speed of the transport members decreases and vice versa. This allows the combined transport members and balancing means to be run at constant torque by a drive motor driving the rotation balancing means and the transport members. Coupling of the transport members to balancing discs allows high speed movement of the sled, for instance at a rate of 550 rpm and a corresponding high rate of variation of the speed of the transport rollers.

Another embodiment of an apparatus for making an absorbent article according to the invention comprises translation-balancing means to maintain a generally constant position of the centre of mass of the combined balancing means, the transport rollers and the sled.

The two transport rollers are connected to a sled which is mounted on the frame so as to be movable relative to the frame, generally parallel to the direction of transport. Preferably the sled is suspended from the frame by a suspension means comprising two vertical arms, a lower end of each arm being connected to a respective end of the sled, each vertical arm being at its upper end hingably connected to the frame.

Allowing the sled to swing on the frame obviates the need for linear bearings, and allows for reciprocation at relatively high frequencies using a simple drive mechanism such as a reciprocating cantilever. Preferably the amplitude of reciprocation of the sled can easily be adjusted by varying the distance between the pivot point of the cantilever at the point of connection of the cantilever to the sled. To the cantilever, a displacement balancing means is connected in the form of for instance a rotary mass balance or a planetary gear box. Balancing both the translational movement of the sled and the rotary movement of the transport rollers, allows the apparatus to be run at high frequencies (above 10 Hz) which is required in efficient disposable diaper manufacture.

BRIEF DESCRIPTION OF THE DRAWINGS

Embodiments of the method and apparatus according to the invention will be described in detail with reference to the accompanying drawings. In the drawings:

FIG. 18 shows a schematic frontal view of a diaper manufacturing line comprising the apparatus according to the invention, FIGS. 19a and 19b show schematic side views of the applicator means for imparting regions of extensibility to the web, FIG. 20 shows a plan view of a diaper provided with regions of extensibility using the apparatus of FIGS. 19a and 19b, and FIG. 21 shows a schematic side-view of applicator means for depositing absorbent gelling material in an absorbent article.

DETAILED DESCRIPTION OF THE INVENTION

Figure 1:
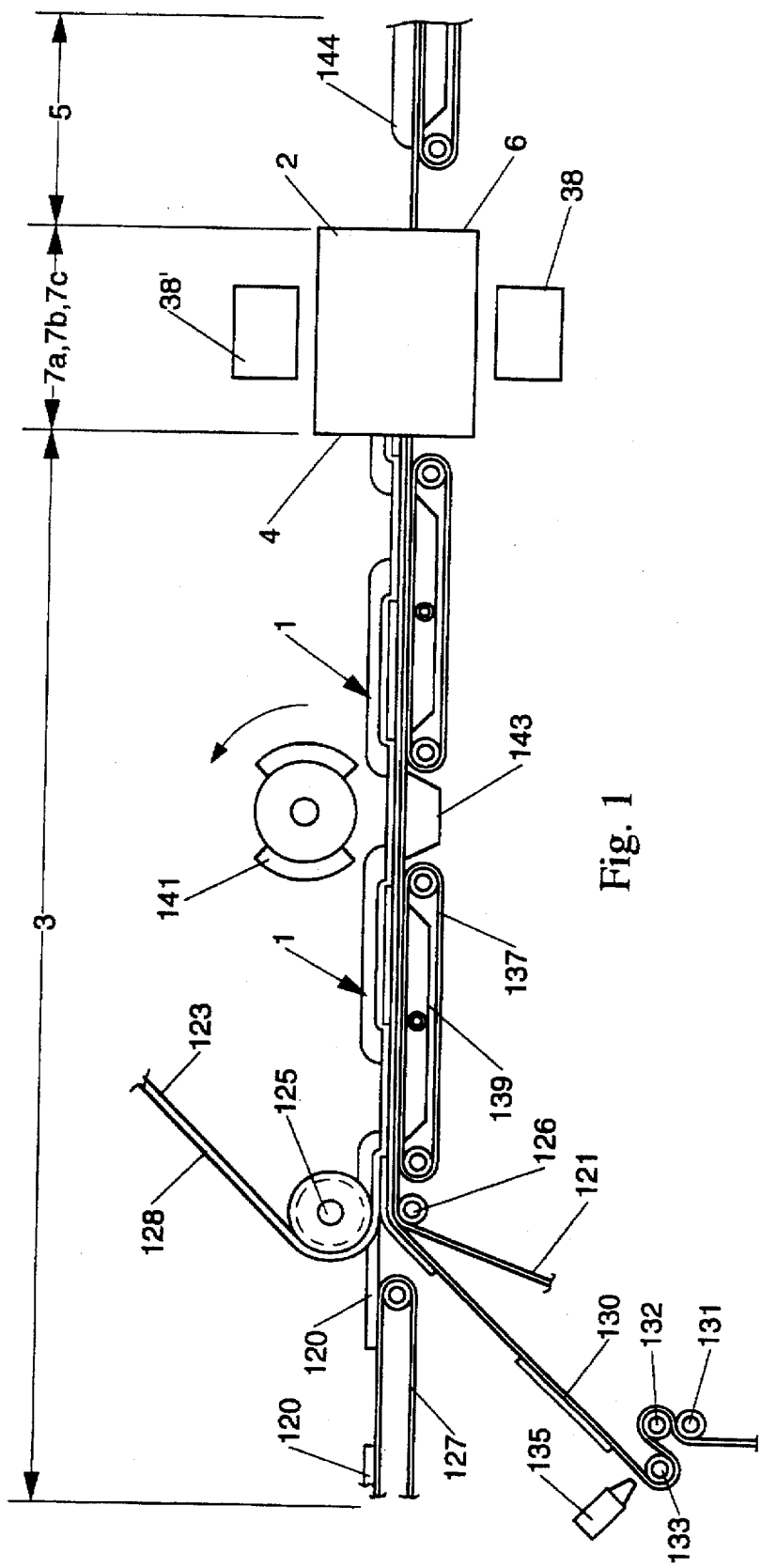
FIG. 1 shows a side elevational view of a production line for the manufacture of an absorbent product.

FIG. 1 shows side-elevational view of a continuous process for making an absorbent product 144. A continuous web 1 is assembled from an absorbent pad element, or core 120, which is encased between a liquid-pervious topsheet 121 and a liquid impervious backsheet 123. The absorbent cores 120 are fed into the nip between a pair of laminating rolls 125,126 at regularly spaced intervals by means of an infeed conveyor 127. In a preferred embodiment, the cores 120 are comprised of airfelt, within a cellulosic tissue envelope, to provide integrity to the core in use. The backsheet 123 is coated on its inner surface with beads or spirals of adhesive 128, for affixing the backsheet to the core 120. Continuous bands of elastic 130 are fed from metering rolls 131, 132 and 133 past a glue nozzle 135. The S-wrap arrangement of the rolls 131, 132 and 133 minimises deformation of the elastic band 130 and allows for accurate control of the speed of the elastic. The elastic bands are fed into the direction of transport, F, at a lower speed than the cores 120, the backsheet 123 and the topsheet 121, so that the elastic bands 130 are stretched. After passing through the combining nip, the web passes onto a perforated vacuum conveyor belt 137. A vacuum suction box 139 draws the web against the conveyor belt 137, to maintain a uniform tension in the elasticised web 1. Excess backsheet 123 and topsheet 121 are removed by rotating trim knife 141 and anvil 143, for instance to form side notches in a diaper. The web 1 is subsequently passed at a constant speed of transport to the infeed side 4 of the apparatus 2 according to the invention, for periodically changing the speed of web. In the apparatus 2, the web 1 can be slowed down, or stopped and is contacted by applicator means 38, or 38'. The applicator means can comprise means for providing a strip of material, such an elastic strand or strip, a waist cap or a strip of reinforcement material in the cross-machine direction, i.e., the direction which is perpendicular to the direction of transport F and which is perpendicular to the plane of the drawing. The applicator means 38,38' can be located on the side of the topsheet 121 or on the side of the backsheet 123. The latter is useful if a reinforcement strip is attached to the backsheet, which reinforcement strip serves as a landing member for refastenable adhesive tape fasteners. A reinforcement strip of this kind has for instance been described in European patent EP-B- 0 286 030.

The web 1 leaves the outfeed side 6 of the apparatus 2 at the constant web speed. The speed of the web portions located upstream and downstream from the apparatus 2 along upstream trajectory 3 and downstream trajectory 5 is not affected by the change in speed of those parts of the web 1 that are passing through the apparatus 2.

Figure 2:
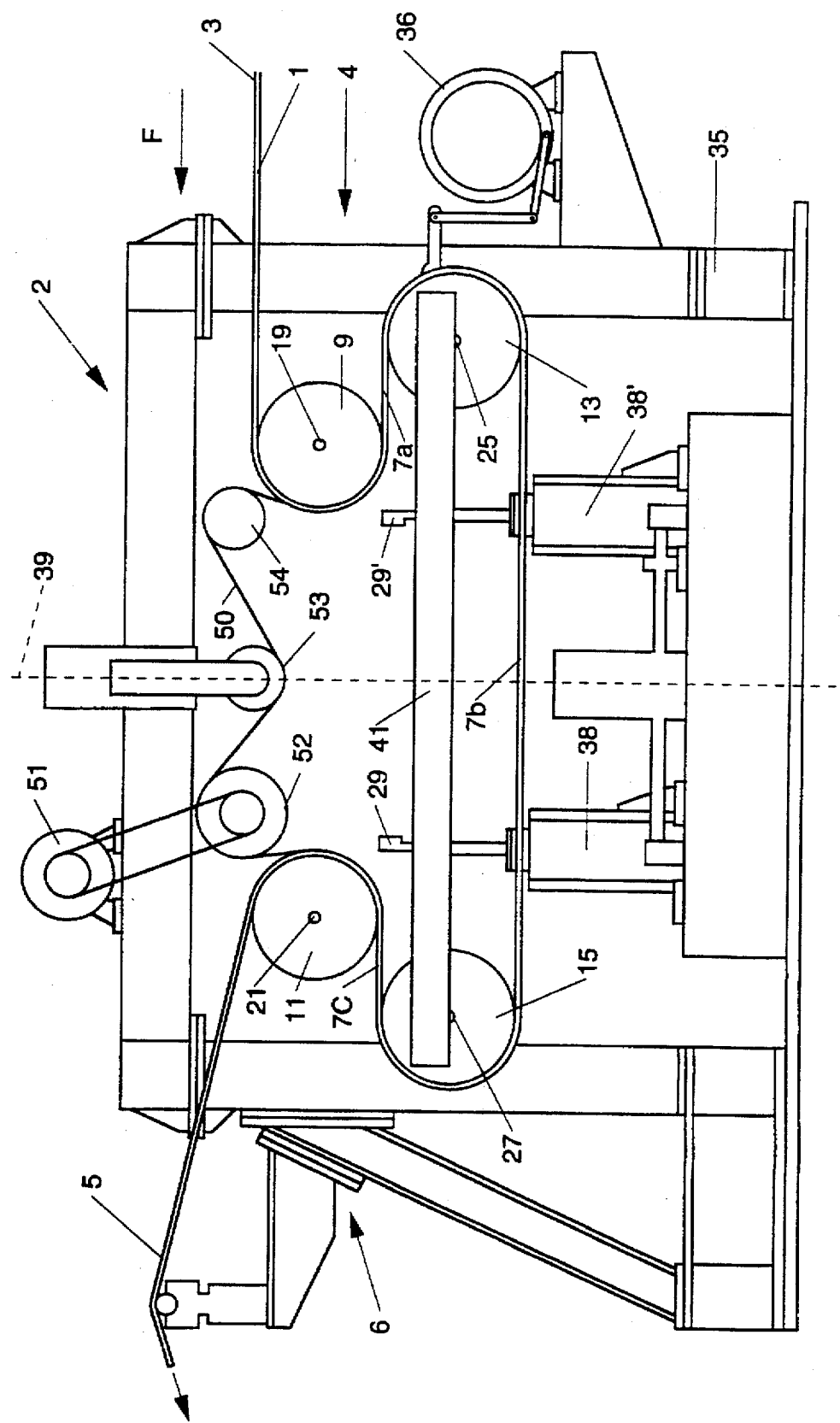
FIG. 2 shows a schematic side elevational view of an embodiment of the apparatus according to the invention, FIGS. 3a, 3b and 4 schematically show embodiments of an apparatus according to the invention, wherein the intermediate trajectory is translated.

FIG. 2 shows the apparatus 2 for changing the speed of a flexible web 1 of relatively low tear strength. With flexible, it is meant that the web 1 can be transported along a curvilinear trajectory and will adapt its shape so as to conform to the trajectory. The web 1 is formed of flexible material, such as paper, airfelt, plastic etc. and can be comprised of the core 120, the topsheet 121, the backsheet 123 or any combination thereof.

The web 1 is transported along upstream trajectory 3 with a constant velocity of transport, $V_0$, in the machine direction F. The upstream trajectory 3 is formed by the length of the web 1 which extends to the right of the first guide roller 9 in FIG. 2, and which is moving towards the infeed side 4 of the apparatus. After passing through the apparatus, the web 1 exits at the outfeed side 6 and is transported at constant velocity $V_O$ along the downstream trajectory 5, which extends to the left of the guide roller 11. The upstream and the downstream trajectories need not correspond to the machine direction, and can be formed by straight-line or curvilinear paths.

The guide rollers 9 and 11 are rotationally connected to the frame 35. The guide rollers 9,11 have a fixed position. The web 1 is looped around an upstream and a downstream transport roller 13,15 which are mounted on a sled 41. The sled 41 is cyclically translated along the frame 35, generally parallel to the machine direction F, by drive motor 36.

An intermediate trajectory 7a, 7b, 7c of the web 1 is located between the upstream guide roller 9 and the downstream guide roller 11, and comprises a first section 7a and a third section 7c, of variable length, located between the upstream guide roller 9 and the upstream transport roller 13 and the downstream transport roller 15 and the downstream guide roller 11 respectively. The second section 7c of the intermediate trajectory 7 is located between the transport rollers 13 and 15 and is of constant length.

Because of the symmetry of the intermediate trajectory 7a, 7b, 7c, the increase in length of the first section 7a, upon displacement of the sled 41 opposite to the machine direction F and away from the equilibrium position 39, is compensated by an equal decrease in length of the third section 7c, and vice versa. As the length of the second section 7b is constant, the whole intermediate trajectory 7 is of constant length. Hence the time for the web 1 to travel past the intermediate trajectory 7a, 7b, 7c is independent of the position of the sled 41 with respect to the frame 35.

When the part of the web that is located along the second section 7b of the intermediate trajectory 7a, 7b, 7c, is stationary relative to the frame 35, the web 1 is contacted by applicator means 29, 29', 38, 38' which positionally stationary with respect to the frame 35. The applicator means comprise a pair of vertically displaceable tampers 29, 29' which press the web 1 against the lower parts 38, 38' of the applicator means. After the applicator means have interacted with the web 1, the web is accelerated along the section 7b of the intermediate trajectory towards the outfeed side 6 of the apparatus 2, and is supplied to the downstream trajectory 5 with web speed $V_O$.

The guide rollers 9,11 and the transport rollers 13,15 are driven by a drive member in the form of a closed loop 50 and pulleys 52,53 and 54. The loop 50 is partly parallel to the intermediate trajectory 7a, 7b, 7c. The loop 50 is driven at a constant speed which is equal to the speed of transport, $V_O$, of the web 1 by a single drive motor 51. By driving the guide rollers 9,11 and the transport rollers 13, 15, the strain exerted on the web 1 is minimized and can be limited to the acceleration forces, which are acting to change the speed of the web.

Figure 3A:
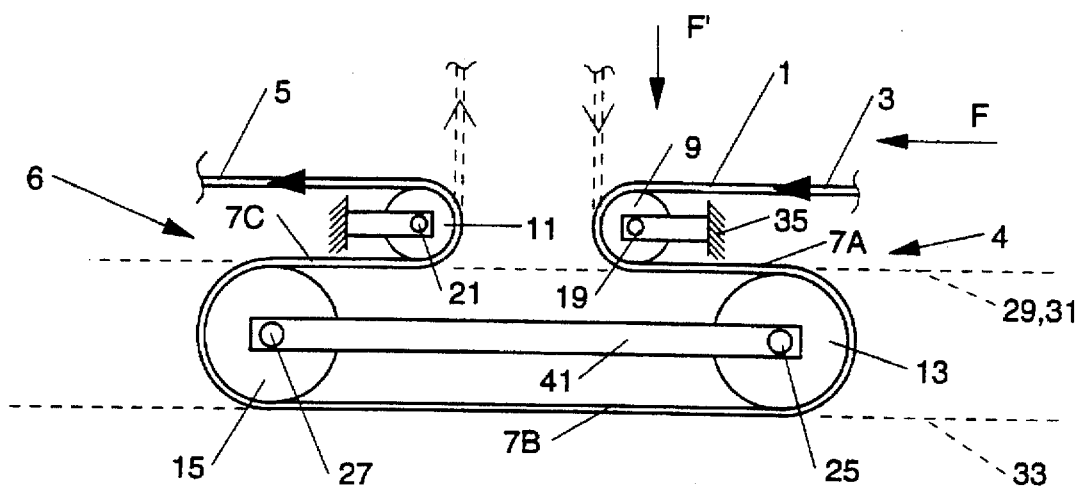
Figure 3B:
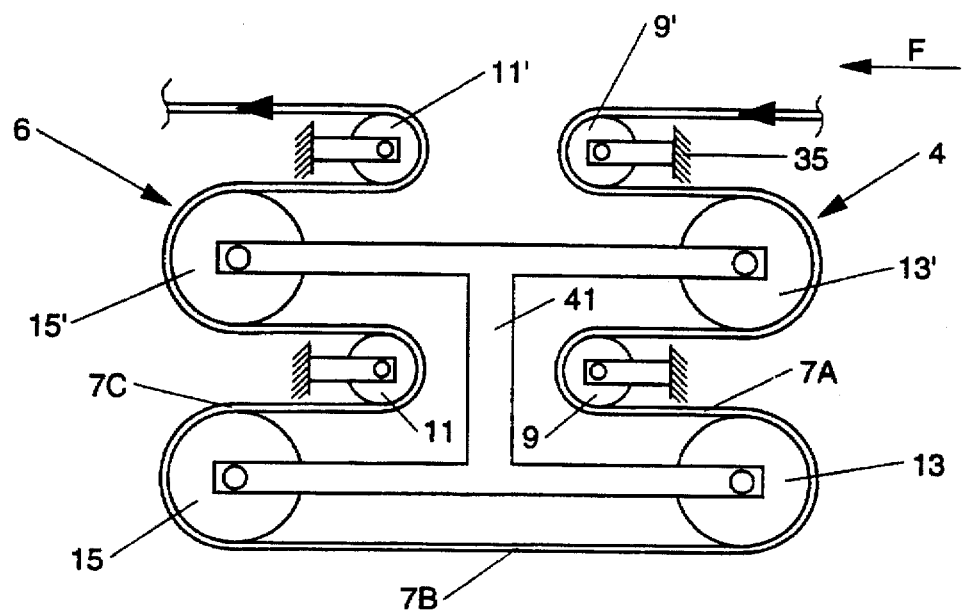
Figure 4:
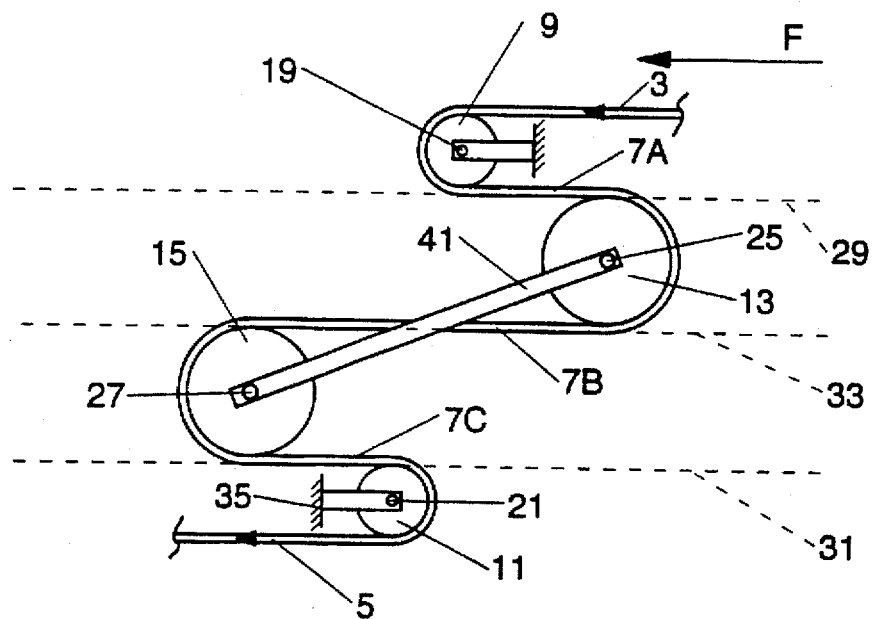

FIGS. 3a,3b and 4 illustrate embodiments in which the intermediate trajectory 7a, 7b, 7c is translated with respect to the stationary frame 35. In the embodiment of FIG. 3a, the guide rollers 9,11 and the transport rollers 13,15 are arranged in a double S-shaped loop in which a left-hand, reverse S-shaped loop comprising the downstream guide roller 11 and the downstream transport roller 15, is connected via its bottom leg to a right-hand S-shaped loop comprising the upstream transport roller 13 and the upstream guide roller 9.

In the embodiment of FIG. 3b, the sled 41 comprises two pairs of transport rollers 13,13' and 15,15'. The intermediate trajectory 7 comprises the part of the web 1 which is located between upstream guide roller 9' and downstream guide roller 11'. The web 1 is stationary relative to the frame 35 along section 7b of the intermediate trajectory 7 when the sled 41 moves against the direction of transport, F, with a velocity of $V_O/4$. The addition of n pairs of guide rollers to the frame 35 and n pairs of transport rollers to the sled 41, allows the speed of the sled 41 to be reduced to $V_O/2n$ to stop the motion of the web 1 along section 7b. Hence, the web 1 can be run at a relatively high speed, while maintaining the speed of the sled 41 relatively low, although the construction of the sled becomes more complicated upon addition of extra pairs of transport rollers.

In the embodiment of FIG. 4, the transport rollers and the guide rollers are configured in an upper and lower S-shaped loop. Upon displacement of the sled 41 in the upstream direction (opposite to the direction of transport, F), parallel to the sections 7a,7b and 7c, the first section 7a of intermediate trajectory is elongated. Generally the direction of displacement of the sled 41 will correspond to the direction of transport, F, in which the web 1 is transported towards the input side 4 of the apparatus. However, as is indicated in FIG. 3a, the web 1 can be transported towards the input side 4 and away from the output side 6 at any desired angle, the direction F' being for instance vertical as indicated by the broken lines in FIG. 3a.

A part of the incoming web is stored along the increased length of section 7a. The parts of the incoming web that cannot be accommodated along the increased length of section 7a, slip past the upstream transport roller 13, via the downstream transport roller 15 and guide roller 11 to the downstream trajectory 5. At the downstream side, the section 7c is shortened by the same amount by which section 7a is increased. The length of web located along the decreased length of section 7c is also passed to the downstream trajectory 5.

When the sled 41 moves against the direction of transport F at a speed $V_T$, the increase in length of the section 7a in a predetermined time interval, is proportional to $V_T$ m. In the predetermined time interval, the length of incoming web 1 is proportional to $V_O$ m, wherein $V_O$ is the constant velocity of transport of the web 1 along the upstream and downstream trajectories 3, 5. The rate at which the web slips past the upstream transport roller 13 in the direction of transport, is equal to $V_O$–$V_T$, which is the relative speed of the web 1 with respect to the sled 41 and the transport rollers 13,15. As the sled 41 moves at a speed $V_T$ against the direction of transport, the relative velocity of the web,$V_W$, relative to the stationary frame 35 is equal to $V_O$–$2V_T$.

At the downstream side, the decrease in length of section 7c is proportional to $V_T$ m. This length of web is supplied to the downstream trajectory 5. Also supplied to the downstream trajectory 5 is the length of web, slipping past the transport rollers, 13, 15 which is proportional to $V_O$–$V_T$ m, so that the total length supplied in the pre-determined time interval to the downstream trajectory 5 is proportional to $V_O$ m. Hence, the velocity of the web 1 along the downstream trajectory 5 remains unaltered, and is independent of the speed $V_T$ of the sled 41.

It follows that if the sled 41 moves against the transport direction F, at a speed equal to half the speed of transport of the web 1 ($V_T=V_O/2$), the web 1 travels along the second section 7b of the intermediate trajectory 7 at the same speed at which the section 7b is moved along the frame 35.

Hence, the net displacement of the web along the second section 7b, relative to the stationary frame 35, is zero. If the sled 41 moves against the transport direction at a speed $V_T$ which is slower than half the speed of transport, $V_o/2$, the web 1 is slowed down relative to the frame 35, along the second section 7b of the intermediate trajectory 7a, 7b, 7c. If the sled 41 moves at a speed, $V_T$, faster than half the speed of transport, $V_o/2$, the speed of the web along the second section 7b of the intermediate trajectory 7 is reversed relative to the stationary frame 35, and is directed against the transport direction. F.

Upon reversal of the speed of the sled 41 in the direction of transport F, the length of section 7a is in a pre-determined time interval shortened by a length which is proportional to $V_T$ m. This length of web, as well as a length proportional to $V_o$ m of incoming web, travels past section 7b of the intermediate trajectory 7. As section 7b itself travels at $V_T$ m/s past the frame 35, the speed of the web 1, VW, relative to the stationary frame 35 equals $V_o+2V_T$ in the direction of transport, F. At the downstream side, the section 7c has increased by a length which is proportional to $V_T$ m.in the pre-determined time interval. This length of web, as well as a length proportional to $V_o$ m that is to be transported to the downstream trajectory 5, needs to be supplied past downstream transport roller 15. Hence the speed with which the web needs to be supplied past the downstream transport roller 15, corresponds to the speed of the web along section 7b ($V_o+V_T$ m/s).

Figure 5:
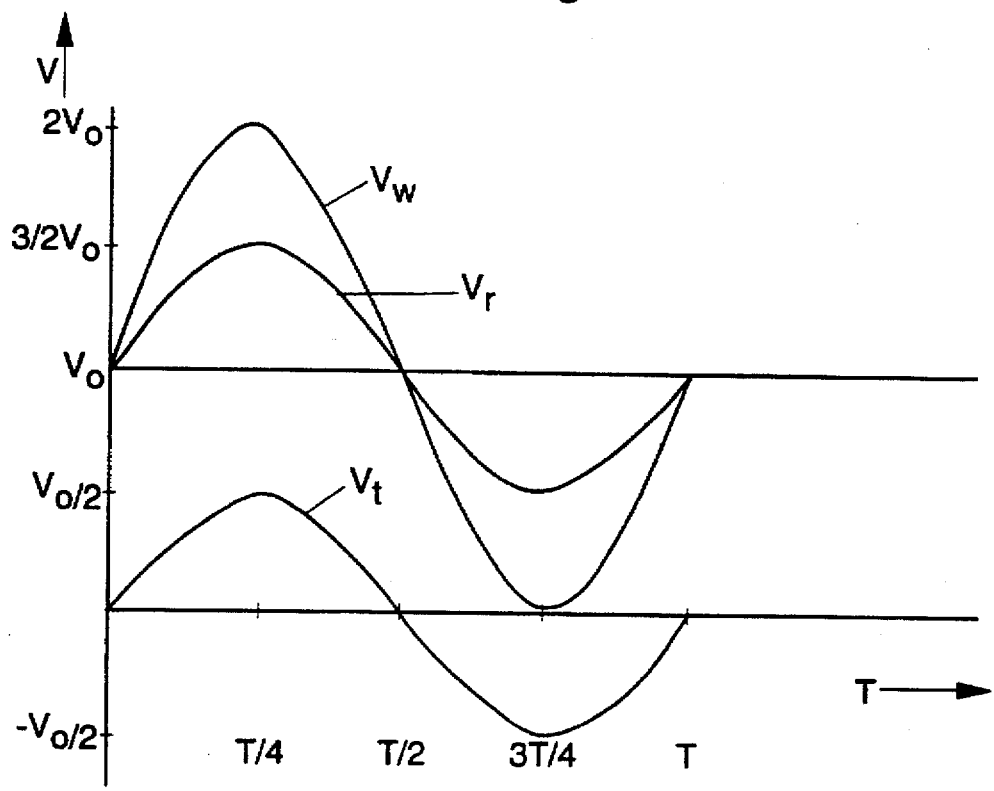
FIG. 5 shows the speed of the sled, transport rollers and web in the apparatus of FIGS. 3a and 4, FIGS. 6 and 7 schematically show embodiments of the apparatus according to the invention wherein the intermediate trajectory is translationally stationary.

In FIG. 5 the speed of the web 1 relative to the stationary frame, $V_W$, along the second section 7b of the intermediate trajectory 7, has been graphically indicated for a cyclical speed of the sled 41, $V_T$, with an amplitude $V_o/2$, equal to half the velocity of transport. The speed of the web relative to the second section 7b of the intermediate trajectory 7 has been indicated as $V_R$. $V_R$ corresponds to the circumferential velocity of the transport rollers 13 and 15. It can be seen that the speed of the web $V_W$ along section 7b, relative to the stationary frame, is in phase with the speed $V_T$ of the sled 41 and varies around the constant speed of transport $V_o$ between 0 and twice the constant speed of transport. The circumferential speed of the transport rollers is also in phase with the speed of the sled 41 and varies around $V_o$ between $V_o/2$ and $3V_o/2$.

Figure 6:
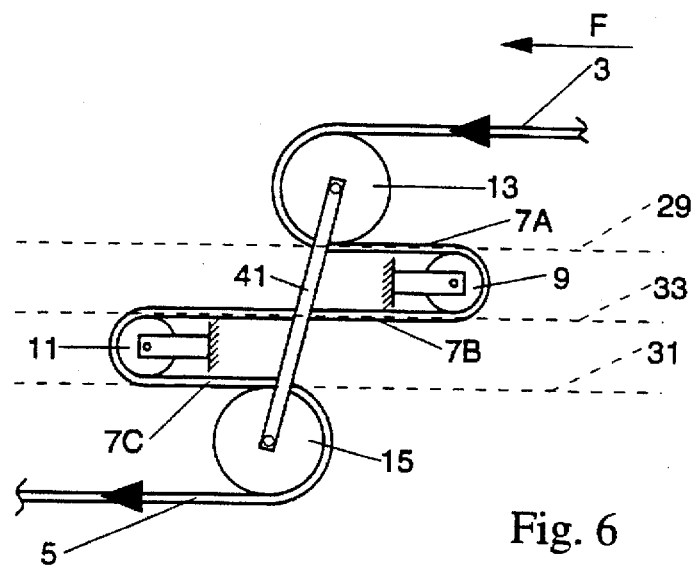
Figure 7:
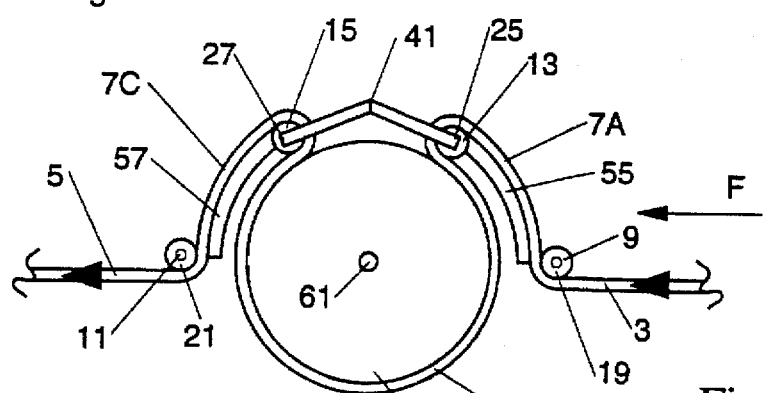

FIGS. 6 and 7 show embodiments of the apparatus 2 in which the second section 7b of the intermediate trajectory 7 is translationally stationary relative to the frame 35.

Moving the sled 41 in FIG. 6 in the transport direction F at half the speed of transport, causes the upstream trajectory 3 and the section 7a to be increased in length. The incoming web 1 is stored along this increased length, so that the speed of the web along section 7b is stationary. At the same time, the downstream trajectory 5 and the section 7c are shortened, and the parts of the web that were located along these sections are supplied to the downstream trajectory 5.

Reversal of the movement of the sled, causes the web that was located along the increased lengths of the upstream trajectory 3 and section 7a, to be accelerated along section 7b to the downstream side 5.

The embodiment of the method and apparatus as shown in FIG. 7 works according to the same principles as the embodiment of FIG. 6. In FIG. 7, the sections 7a and 7c of the intermediate trajectory 7, are located on a first cylindrical surface along transport roller extension means 55, 57. The second section 7b of the intermediate trajectory 7 is located on the surface of a drum 59. Upon moving of the sled 41 concentrically with the axis 61 of the drum 59, in an anticlockwise direction, the lengths of the section 7a and the upstream part of section 7b are increased. The lengths of the downstream side of section 7b and the third section 7c are decreased in length such that the combined length of sections 7a and 7c as well as the length of section 7b is constant.

When the transport rollers 13,15 are moved with the sled 41 in a predetermined time interval along a section of the circumference of the drum 59 which is proportional to half the velocity of transport, about half the incoming web is stored along the increased length of section 7a and about half the incoming web is stored along the increased upstream part of section 7b. The velocity of the web along section 7b, relative to the frame is constant.

Figure 8:
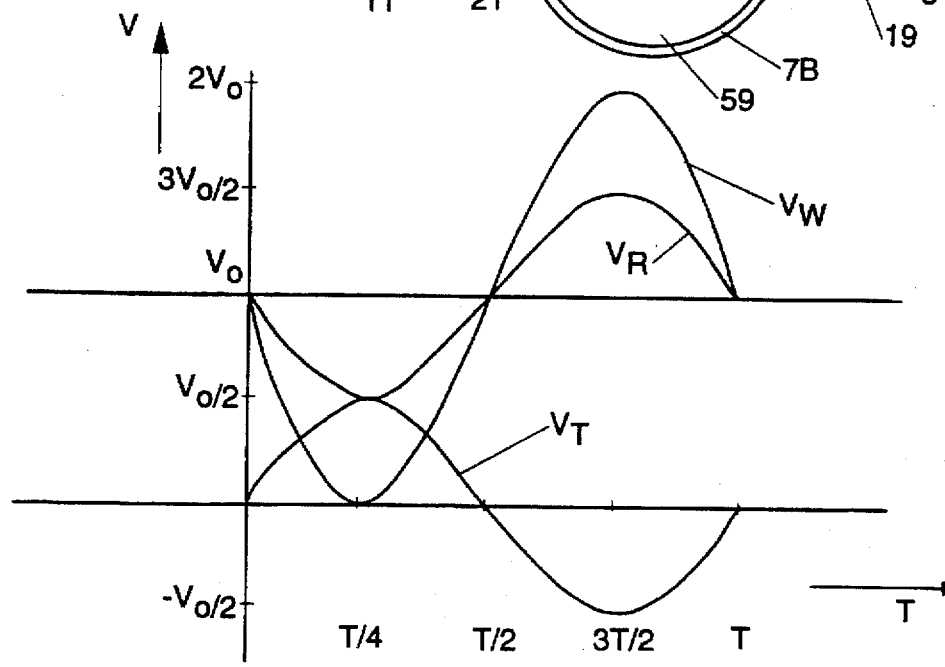
FIG. 8 shows the speed of the sled, transport rollers and web in the apparatus of FIGS. 6 and 7.

In FIG. 8, the web speed, $V_W$ along section 7b and the circumferential speed $V_R$ of the transport rollers 13, and 15 are given for cyclic displacement of the sled 41 along a trajectory concentric with the axis 61 of the drum 59, with a velocity $V_T$ having an amplitude of half the speed of transport of the web. The circumferential speed of the transport rollers is indicated as $V_R$. When the drum 59 is rotationally connected to the frame, the circumferential speed of the drum will correspond to the web speed, $V_W$. The velocity and phase relationships of FIG. 8 also apply to the embodiment of FIG. 6.

Figure 9:
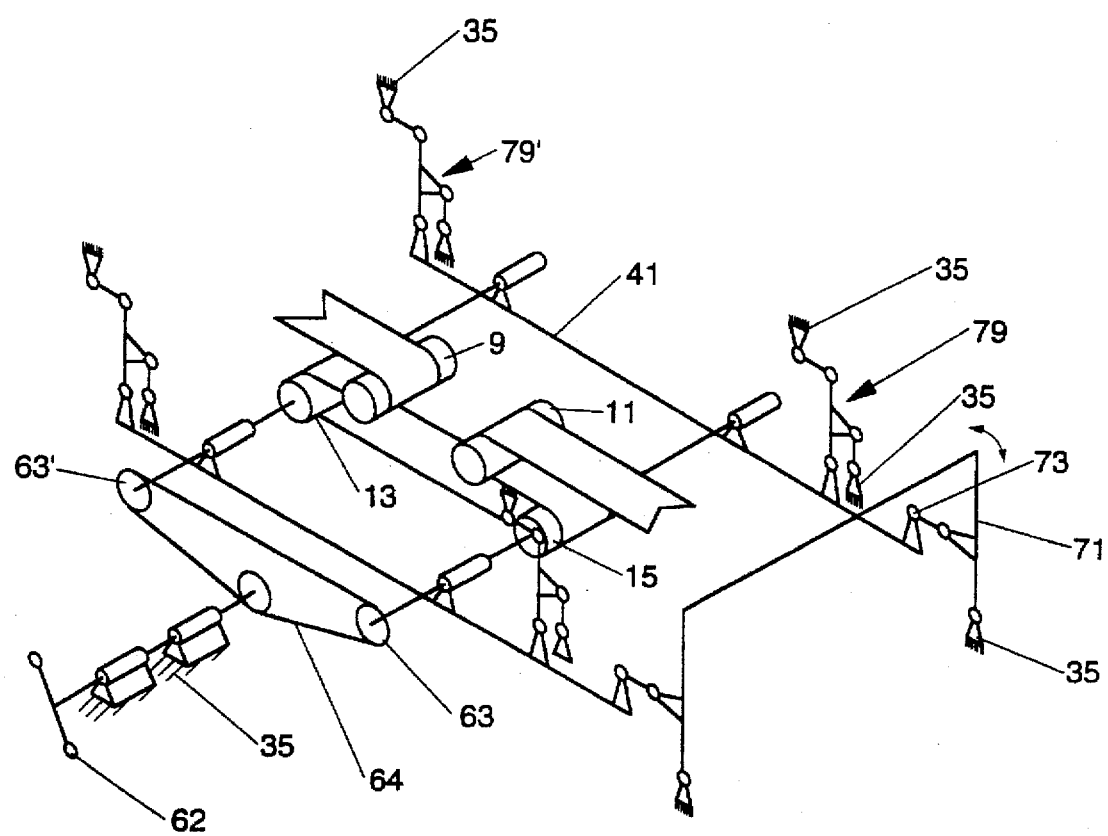
FIG. 9 shows a schematic perspective view of the apparatus according to the invention.
Figure 10:
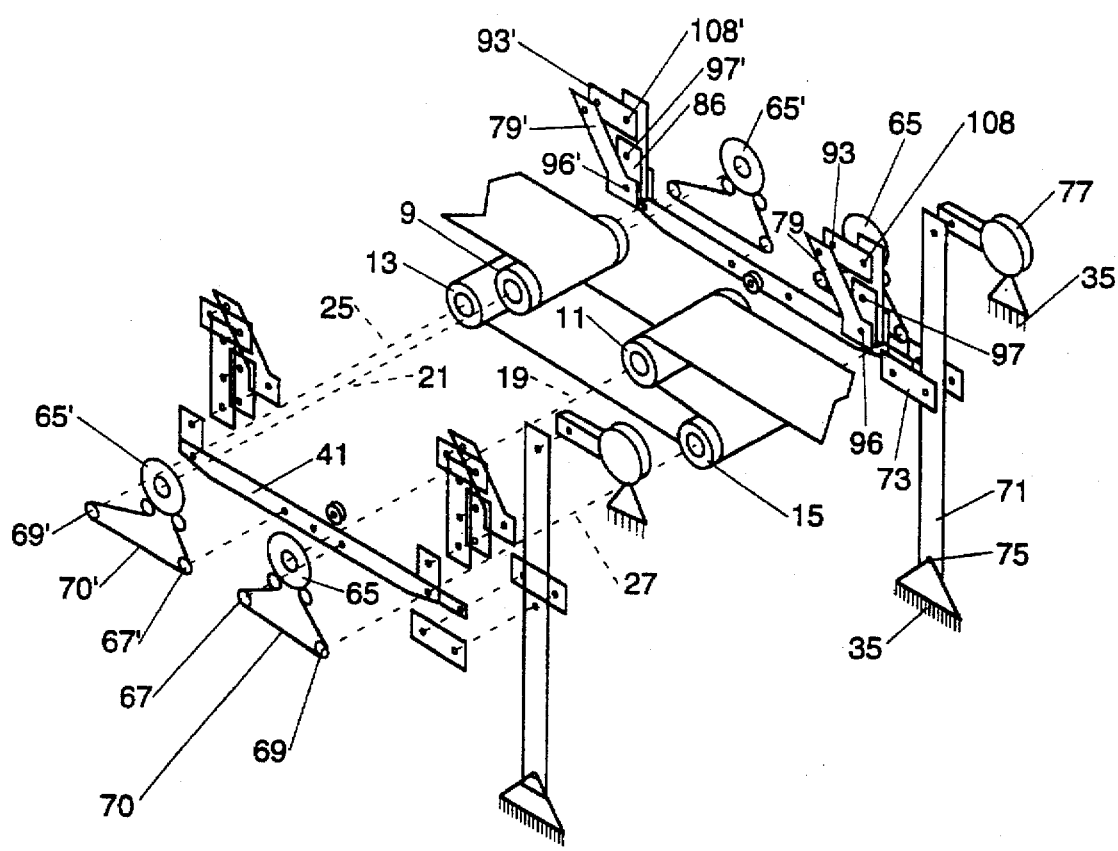
FIG. 10 shows a schematic perspective view of the translation-balancing means and the rotation-balancing means, FIG. 11a and 11b schematically show the functioning of the rotation-balancing means

FIGS. 9 and 10 show a perspective view of the embodiment of the apparatus in which the guide rollers 9, 11 and the transport rollers 13, 15 are rotationally mounted on the sled 41. The sled 41 is suspended from the frame 35, which has been schematically indicated in these figures, via suspension means 79,79'. The sled 41 is driven by a cantilever 71, which is pivotably connected to the sled in a drive point 73. The transport rollers 13,15 are connected to rotation-balancing means 63,63' which allow the transport rollers to be driven at a constant torque. In the embodiment of FIG. 9, the rotation-balancing means drive a rotating balancing mass 62 via a closed loop member such as belt or chain 64. The rotation-balancing means 63,63' rotate with the same rotational velocity as the transport rollers to which they are connected, and are simultaneously translated within the closed loop member 64. As a consequence the balancing mass 62 is rotated in synchronism with the transport rollers but in the opposite direction to the direction of rotation of the transport rollers. Hence the resultant torque of the balancing mass 62 and the transport rollers 13,15 is constant.

In a preferred embodiment of the invention, the rotation balancing means 63,63' each comprises a disc 65, 65' which is rotatably connected to the frame 35. This is shown in FIG. 10. For each disc 65, 65' two pulleys 67,69 and 67 and 69' are mounted on the sled 41. A belt 70,70' is looped around the balancing diso's 65, 65' and the pulleys 67, 69, 67', 69'. The pulleys 69,69' are each coupled to the axes 25,27 of the transport rollers, 13,15. The circumferential speed of the pulleys 69,69' is equal to $V_R$.r/R wherein r is the radius of the pulleys 69,69' and R is the radius of the transport rollers 13,15.

Figure 11A:
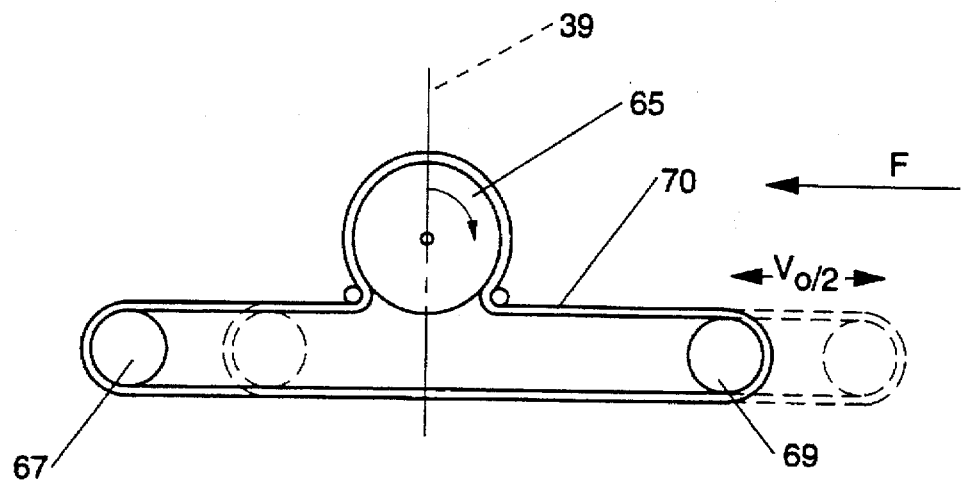
Figure 11B:
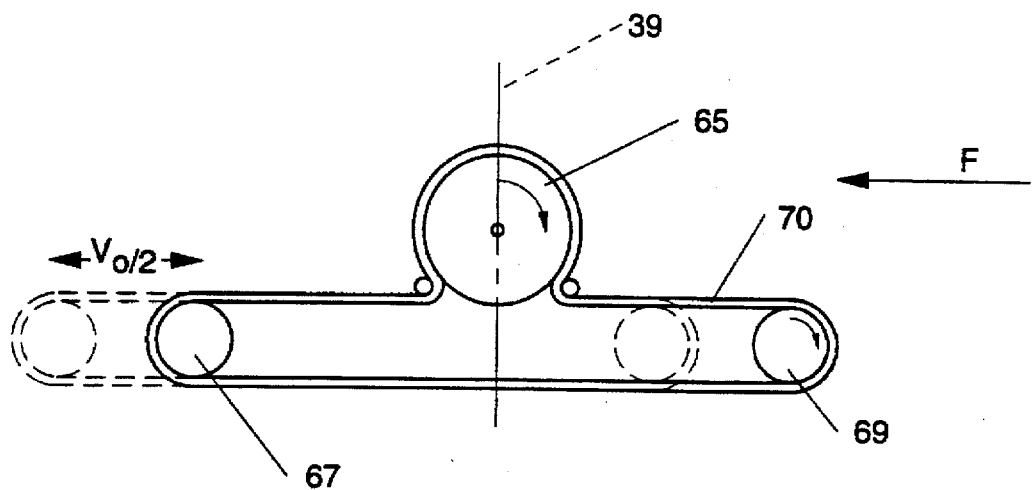

The functioning of the balancing means 63,63' as shown in FIG. 10 has been schematically indicated in FIGS. 11a and 11b. In FIGS. 11a and 11b, the position of the sled 41, has been indicated at its equilibrium position 39 in solid lines and at a position close thereto, in broken lines.

When the sled 41 is furthest from its equilibrium position 39 (a position which has not been indicated in FIGS. 11a and 11b), the sled 41, and with it the pulleys 67,69, are translationally stationary. The stationary positions of the sled 41 for the embodiments of FIGS. 3a, 3b and 4, can be found in FIG. 5 at positions 0, T/2 and T of the x-axis. For a stationary sled 41, the belt 70 is driven by pulley 69 such that the circumferential speed of the disc 65 in this case is equal to the circumferential speed of the pulley 69. When the speed of the sled 41, $V_T$, is zero, it can be seen from FIG. 5 that the circumferential speed of the transport rollers, $V_R$, is equal to the speed of transport, $V_0$. For the case in which the radii of the pulleys 69, 69' are equal to the radii of the transport rollers 13,15, the circumferential speed of the disc 65 equals $V_0$.

When the sled 41 is close to its equilibrium position 39, and is moved in the direction of transport, F, from the position indicated by the broken line in FIG. 11a, to the position indicated by the solid line in FIG. 11a, the speed of the sled approximately equals $V_0/2$. This situation can be found around time T/4 on the x-axis of FIG. 5. When pulleys 67 and 69 are in a pre-determined time interval displaced by a distance proportional to $V_0/2$, a length of belt 70 proportional to $V_0$ (the broken-line part at the right-hand side in FIG. 11a) needs to be transported past pulley 69 to pulley 67 to take up the slack. No rotation of the disc 65 is necessary. However, as can be seen from FIG. 5, the rotational speed of the transport rollers and the pulleys that are driven by the transport rollers, equals $3V_0/2$. Therefore, in addition to the length $V_0$ of belt 70 that is moved past the pulleys 67 and 69 upon translation of the pulleys, an additional length $V_0/2$ of belt 70 needs to be supplied to pulley 69 by rotation of the belt 70 past the disc 65. Hence the rotational speed of the disc 65 equals $V_0/2$.

When the sled 41 is close to its equilibrium position, and is moved against the direction of transport F, the speed of the sled again about equals $V_0/2$. This situation is found around time 3T/4 on the x-axis of FIG. 5, and is illustrated in FIG. 11b. Considering again a displacement of the pulleys 69 and 67 proportional to $V_0/2$ in a pre-determined time interval, it can be seen that a length of belt 70, proportional to $V_0$ needs to be taken up by rotation of disc 65. From FIG. 5 it can be seen that the speed of the pulley 69, which is driven by the transport roller 15, equals $V_0/2$, so that in the given time interval an additional length of belt 70, proportional to $V_0/2$, is accumulated at the upstream side of pulley 67. Therefore, in addition to the length proportional to $V_0$ that is to be passed from pulley 67, via the disc 65, to pulley 69, the pulley 67 supplies a length of belt 70 to disc 65 which is proportional to $V_0/2$. Hence the speed of rotation of the disc 65 is proportional to $3V_0/2$.

As appears from the foregoing discussion, the rotation of the disc 65 varies cyclically around the average speed, $V_0$, with a amplitude of $V_0/2$ and has a fixed 180° phase difference with the speed of rotation of the transport rollers 13,15. Only when the radii of the pulleys 67,69 are equal in length to the radii of the transport rollers 13,15 will the amplitudes of the circumferential speed of the disc 65 be equal to the speed of the transport rollers, $V_R$. By adapting the mass distribution of the discs 65 to the moment of inertia of the transport rollers, the overall variations in torque of the combined transport rollers 13,15 and the discs 65, 65' with respect to an axis of the drive motor 51, can be minimized. Hence the drive motor 51 will not be adversely affected by the high-frequency changes in rotational velocity of the transport rollers.

Figure 12:
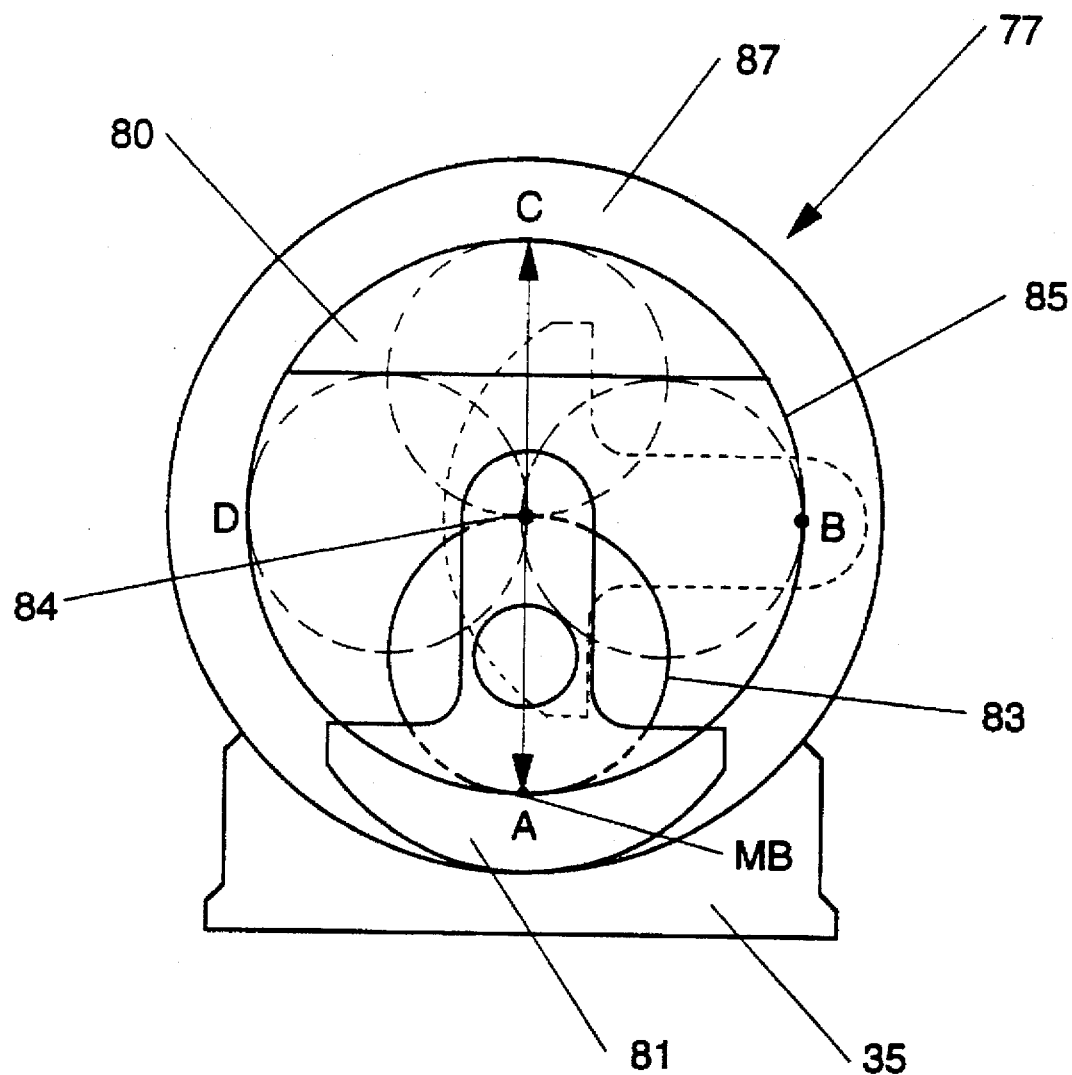
FIG. 12 shows a side-elevational view of the translation-balancing means, FIGS. 13a–13d schematically show the functioning of the translation-balancing means, FIG. 14 schematically shows the funcitoning of the suspension means carrying the sled.

FIG. 12 shows a side-elevational view of the sled-balancing means 77, which is formed by a rotating mass balance that comprises two rotating balancing masses 80,81. The sled balancing means 77 comprises a housing 87 having an inner circular track 85. The housing 87 is attached to the frame 35, and is stationary with respect to the frame. The cantilever 71 is at its upper end connected to the balancing masses 80 and 81.

Rotating mass 80 compensates the inertia forces that are exerted on the cantilever 71 by the sled 41, such that the sled, the cantilever and the balancing means can in combination be driven at a constant force. The sled 41 performs a horizontal periodic motion, and is accelerated and decelerated by the cantilever 71. The sled 41 exerts a periodic force on the cantilever 71 that is proportional to the acceleration and that is largest when the speed of the sled is 0. The horizontal component of the force exerted on the cantilever 71 by the rotating mass 80 is also periodic and has the same frequency as the frequency of reciprocation of the sled 41, is equal in magnitude to the force exerted by the sled and is directed in the opposite direction. The mass 80 is driven, for instance by a drive shaft 84, at a constant rotational speed. The vertical component of the force exerted by the mass 80 on the housing 87, is compensated by the mass 81, that travels up and down along straight-line path A-C.

The mass 81 is mounted on a disc 83, having a diameter equal to half the diameter of the circular track 85. The disc 83 is rotationally mounted inside the housing 87 and travels along the circular track 85. The disc 83 may be formed by a pinion, the circular circumference 85 being provided with meshing gear teeth. The position of the balancing mass 81 and the disc 85 at position B of the circular track 85, have been indicated in FIG. 11 in broken lines. Further rotation of the disc 85 to position C of the circular track 85, will move the centre of mass MB along the line AC from the centre of the circular track 85 to point C. Further rotation of the disc 83 via position D, back to A, moves the centre of mass MB back along line AC to position A.

In FIGS. 13a–13d it is schematically illustrated how the mass balancing system 77 interacts with the sled 41. The housing 87 comprising the circular track 85 is connected to the frame 35 and is stationary with respect thereto. A drive shaft 84, which extends perpendicular to the plane of the drawing and which passes through the center of the circular track 85, rotates the mass 80 at a constant rotational speed. The disc 83 is at its center rotatably connected to the mass 80 such that upon rotation of the mass 80, the disc 83 is rotated along the track 85.

Figure 13A:
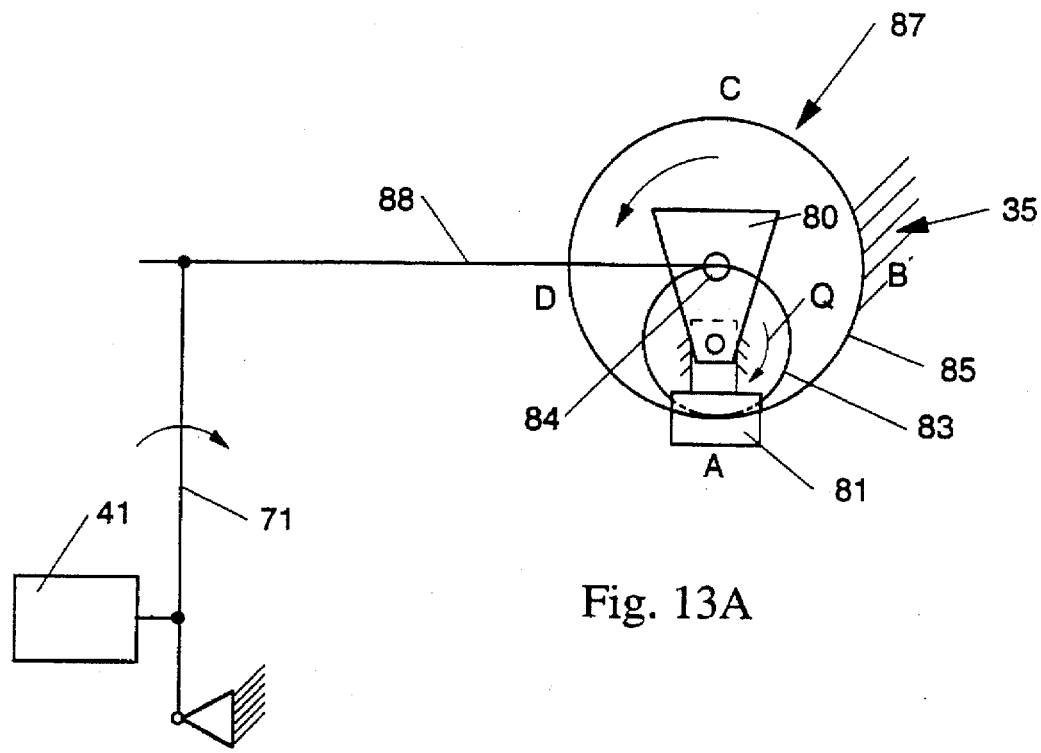

Upon rotation of the disc 83 along the track 85, the points of the circumference of disc 83 that are located in positions corresponding to point A and to the center of the track 85 in FIG. 13a, move along straight-line paths, that are diametrically located with respect to the circular track 85.

Figure 13B:
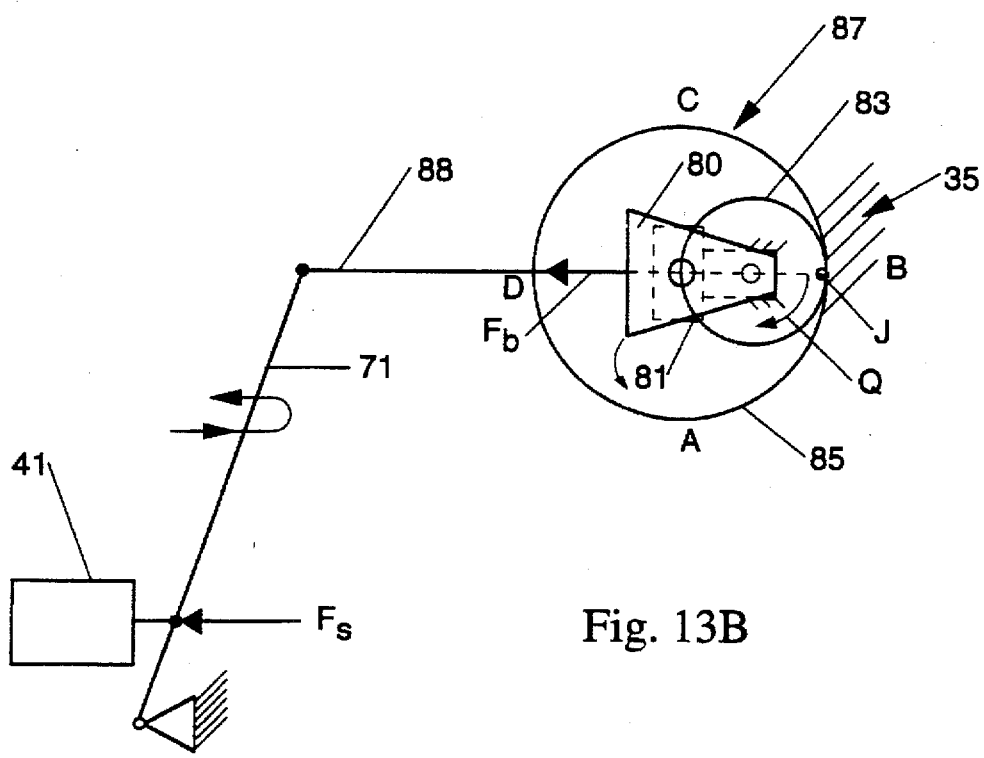
Figure 13C:
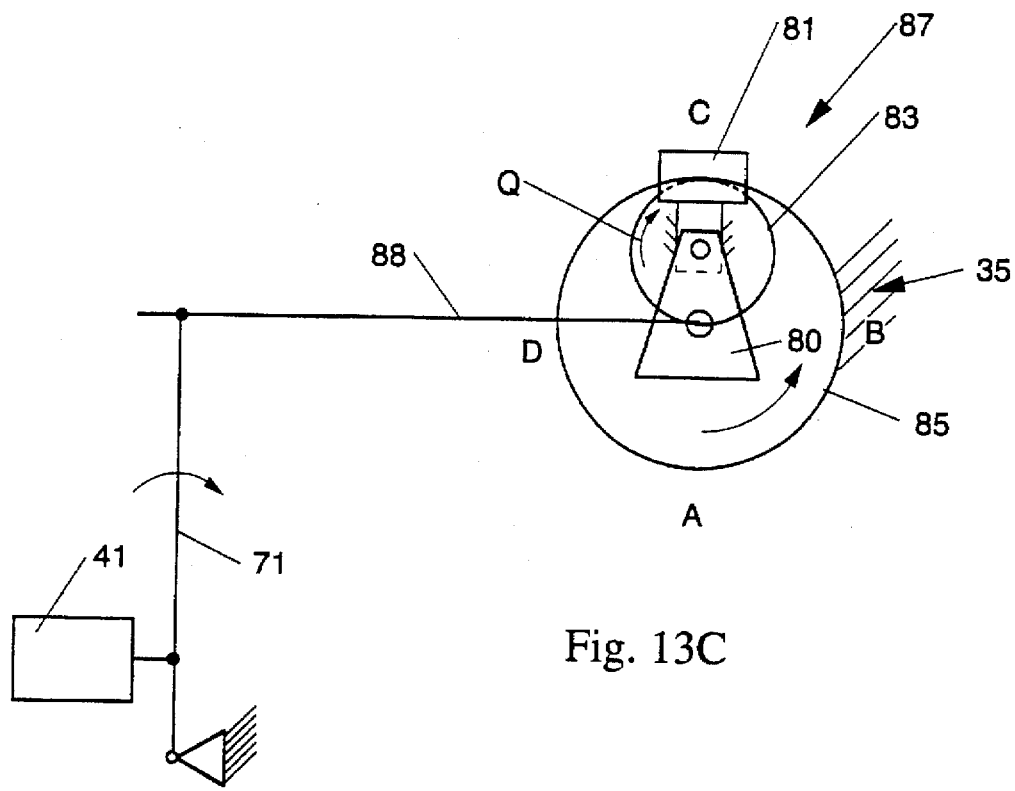

The cantilever 71 is connected to a linkage 88 which is hingeably connected to the circumference of the disc 83 in a point J which in FIGS. 13a and 13c coincides with the center of circular track 85. The drive shaft 84 drives the mass 80 and the disc 83 at a constant rotational speed. As shown in FIGS. 13a and 13c, the sled 41, which has been schematically indicated, is in its equilibrium position. Since the sled 41 is suspended from the frame 35 via suspension means 79, 79', which are preferably formed by a an Evans linkage (which has not been shown in FIGS. 13a–13d), the sled only exerts horizontal inertia forces on point J. As the acceleration of the sled 41 is 0 in its equilibrium position, no horizontal forces are exerted by the sled on point J in this position. The vertical force exerted on the housing 87 by the rotating mass 80, is in the equilibrium position compensated by the force exerted by the mass 81, which is accelerated towards the center of circular track 85.

Upon rotation of the disc 83 in the direction of arrow Q, the point J moves along a straight-line path from the center of the track 85 to point B, as shown in FIG. 13b. The balancing mass 81 moves from position A to the center of track 85. When the cantilever 71 and the sled 41 reach their maximum deflection and the sled is accelerating in the direction of arrow Fs, the horizontal inertia force exerted by the sled on point J is at its largest and is directed opposite to the direction of arrow Fs. The horizontal component of the force exerted on the housing 87 by rotating mass 80 is also at is maximum value and is directed in the direction opposite to arrow Fb, and compensates the force exerted on the point J by the sled 41.

Figure 13D:
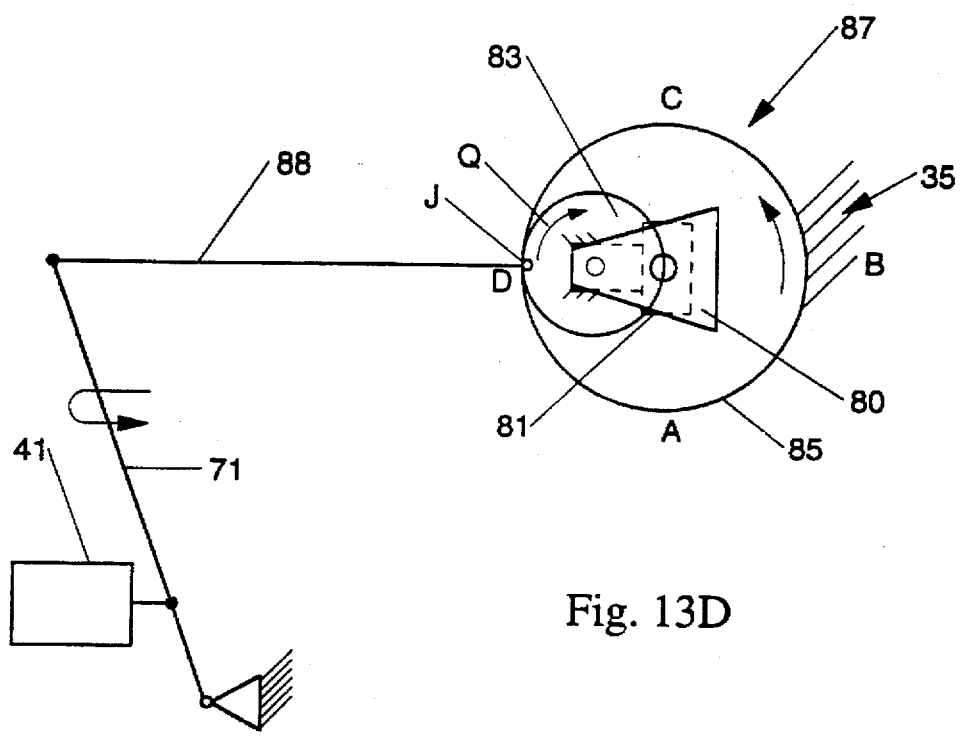

The mass 81, which in FIGS. 13b and 13d has been indicated by the broken lines, is located in the center of circular track 85, and moves in this position at maximum, constant speed. Hence, no inertia force is exerted by the mass 81 on the housing 87.

Upon further rotation of the disc 83, the mass 81 reaches point C, reverses its direction of straight-line movement, and travels back to the center of track 85, as has been shown in FIG. 13c. The forces acting on the housing 87 and point J in FIGS. 13c and 13d are identical in magnitude and opposite in direction to the forces that act in the position of the sled 41 as shown in FIG. 13a and 13b respectively.

The weight of the balancing masses 80,81 and he distances of the balancing masses from the drive shaft 84 will depend on the actual configuration of the sled 41 and the cantilever 71, and can on the basis of the above principles easily be determined. The principle of the mass-balancing of the sled 41 is also applicable to constructions, in which the cantilever 71 is driven by other means than the rotating drive shaft 84.

Figure 14:
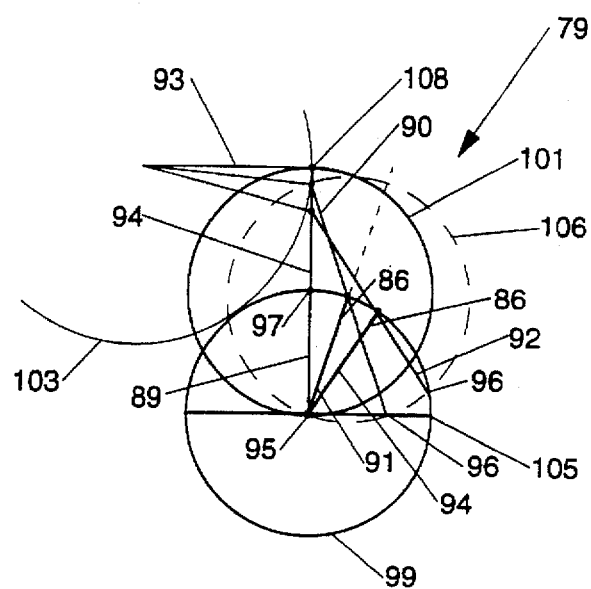

The suspension means 79,79' as shown in FIGS. 9 and 10 comprise a Evans linkage, the principle of which has been schematically indicated in FIG. 14. In the Evans linkage, a vertical suspension arm 89 is suspended in rotation point 97. The sled 41 is suspended at the lower end 96 of the suspension arm 89. Rotation of the vertical suspension arm 89 around the rotation point 97, causes the lower end 96 of the arm 89 to follow a circular rotation path 101. In order to have the lower end of the arm 89 move along a straight-line path 105, the centre of rotation 97' needs to be displaced upon rotation of the arm 89. The suspension arm 89 is thereto connected to a rotation arm 86, which in FIG. 14, for the vertical position of the suspension arm 89, is located behind the suspension arm. The rotation arm 86 is rotatable around rotation point 95, and positions 91 and 94 of the rotation arm 86 have been indicated. The length of the rotation arm 86 is of generally half the length of suspension arm 89.

When the rotation arm 86 is moved to position 91, the lower end of the suspension arm 89 can be located on circular path 106 which is indicated by a broken line. The lower end of the suspension arm 89 will be located on straight-line path 105 for position 91 of the rotation arm 86 when the upper end of the suspension arm 89 is moved vertically downwards. The upper end of the suspension arm 89 is in a hinging point 108 connected to a transverse arm 93. As the transverse arm 93 is of relatively large radius, and the angle of rotation of the arm 93 is relatively small, the path of the hinging point 108, which is part of the circular path 103, approximately corresponds to the vertical displacement of the upper end of the arm 89.

Via the suspension means 79, the sled 41 can be reciprocated along a substantially straight line path 105 without the need for linear bearings. This allows the sled to be reciprocated at a high speed without intensive maintenance requirements to the bearings of the suspension means.

Figure 15:
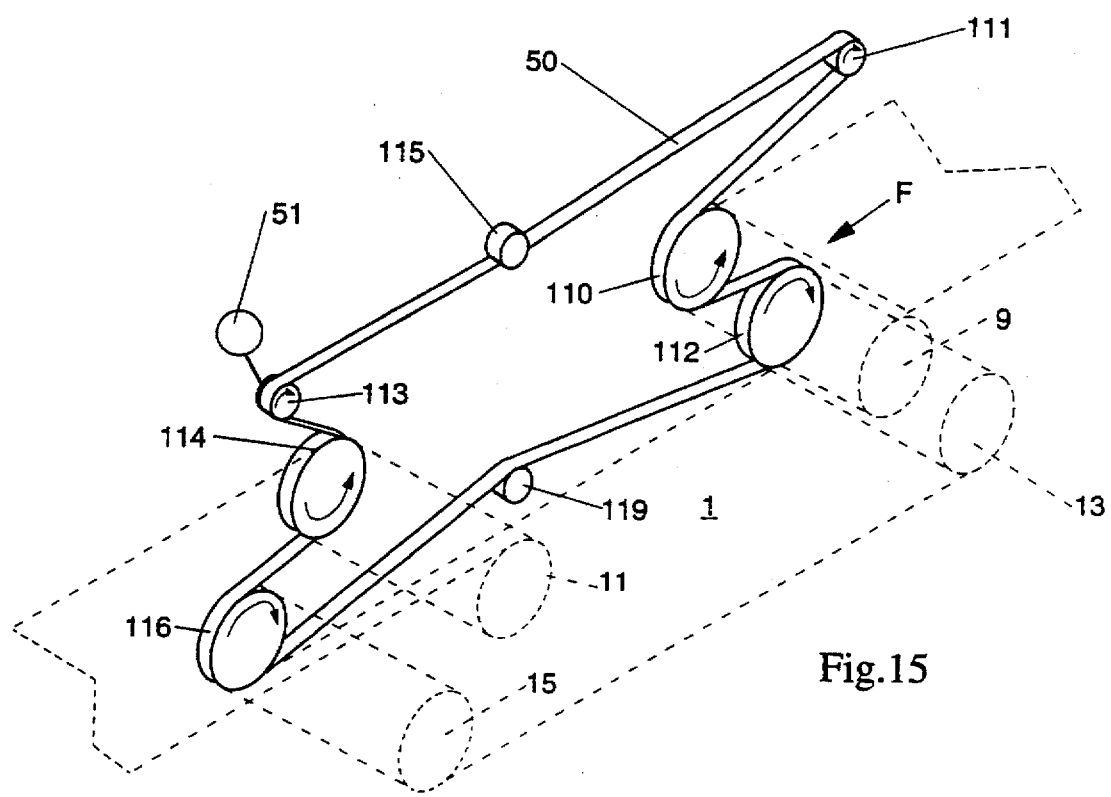
FIG. 15 shows a perspective view of the drive mechanism for rotating the drive rollers and the guide rollers.

FIG. 15 shows a perspective view of the drive mechanism for rotating the guide rollers 9,11 and the transport rollers 13,15 in accordance with the speeds as shown in FIGS. 5 and 8. The drive member 50, which is comprised of a belt, is passed around drive rollers 110, 112, 114 and 116, in a path which is parallel to the web 1. The drive rollers 110 and 114 are equal in diameter to the guide rollers 9 and 11, and rotate at a constant velocity $V_0$ which corresponds to the velocity of the upstream and the downstream parts of the web 1. The drive rollers 112 and 116 are equal in diameter to the transport rollers 13 and 15, and rotate with a cyclic speed of amplitude $V_0/2$ around the speed of transport $V_0$. The belt 50 is passed along pulleys 113 and 111 and forms a closed loop. The pulley 113 is driven by a drive motor, 51, at a constant speed $V_0$. Due to the reciprocation of the transport rollers 13,15, the belt 50 passes along these rollers at the above cyclic speed. The belt 50 drives the guide rollers 9,11 at the constant speed $V_0$.

As used herein, the term "absorbent article" refers to devices which absorb and contain body exudates, and, more specifically, refers to devices which are placed against or in proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use and, preferably, to be recycled, composted or otherwise disposed of in an environmentally compatible manner). A "unitary" absorbent article refers to absorbent articles which are formed of separate parts united together to form a co-ordinated entity so that they do not require separate manipulative parts like a separate holder and liner. A preferred embodiment of an absorbent article of the present invention is the unitary disposable absorbent article, diaper 144, shown in FIG. 16. As used herein, the term "diaper" refers to an absorbent article generally worn by infants and incontinent persons that is worn about the lower torso of the wearer. It should be understood, however, that the present invention is also applicable to other absorbent articles such as incontinent briefs, incontinent undergarments, diaper holders and liners, feminine hygiene garments, and the like.

Figure 16:
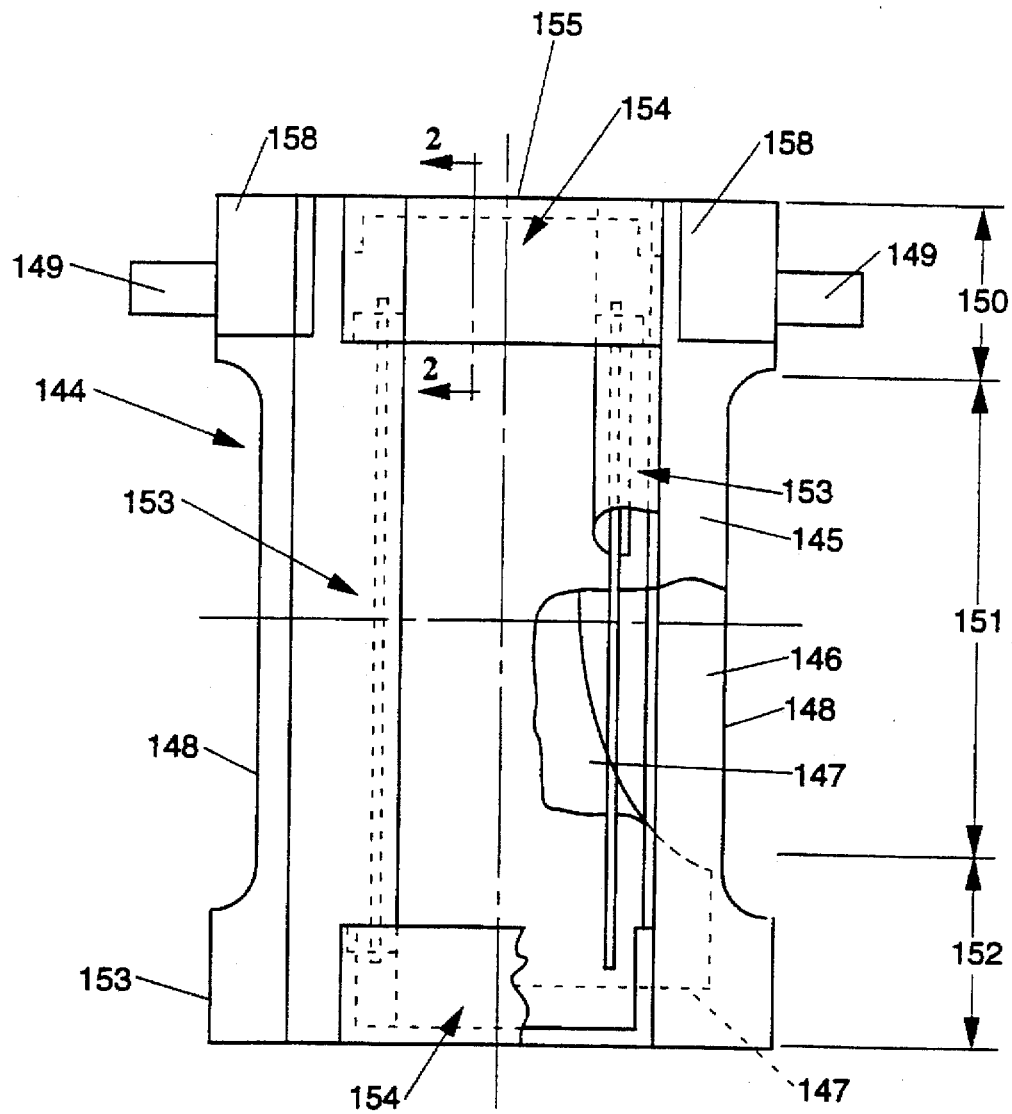
FIG. 16 shows a partially cut-away plan view of an absorbent article.

FIG. 16 is a plan view of the diaper 144 of the present invention in its flat-out, state (i.e., with elastic induced contraction pulled out) with portions of the structure being cut-away to more clearly show the construction of the diaper 144 and with the portion of the diaper 144 which faces or contacts the wearer, the inner surface, oriented towards the viewer. As shown in FIG. 16, the diaper 144 preferably comprises a liquid pervious topsheet 145; a liquid impervious backsheet 146 joined with the topsheet 145; an absorbent core 147 positioned between the topsheet and the backsheet; side panels 148; elasticized leg cuffs 153; an elastic waist feature 154 and a fastening system generally multiply designated as 149.

FIG. 16 shows a preferred embodiment of the diaper 144 in which the topsheet 145 and the backsheet 146 have length and width dimensions generally larger than those of the absorbent core 147. The topsheet 145 and the backsheet 146 extend beyond the edges of the absorbent core 147 to thereby form the periphery of the diaper 144. While the topsheet 145, the backsheet 146, and the absorbent core 147 may be assembled in a variety of well known configurations. Preferred diaper configurations are described generally in U.S. Pat. No. 3,860,003 entitled "Contractable Side Portions for Disposable Diaper" which issued to Kenneth B. Buell on Jan. 14, 1975; and U.S. patent application Ser. No. 07/715, 152, allowed, "Absorbent Article With Dynamic Elastic Waist Feature Having A Predisposed Resilient Flexural Hinge", Kenneth B. Buell et al. filed Jun. 13, 1991; each of which is incorporated herein by reference.

Figure 17:
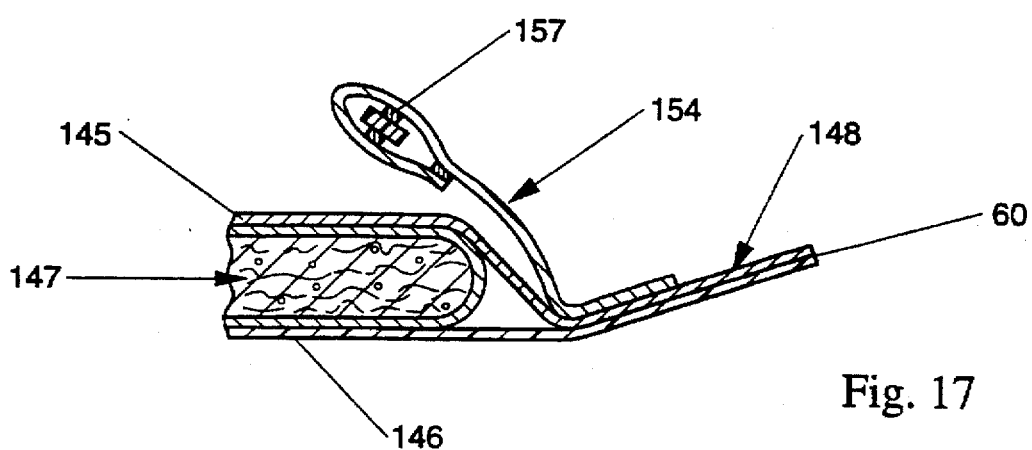
FIG. 17 shows a cross-sectional view of the absorbent article of FIG. 16 along the line 2—2.

FIG. 17 is a cross-sectional view of the diaper 114 taken along section line 2—2 of FIG. 16.

The absorbent core 147 may be any absorbent means which is generally compressible, conformable, non-irritating to the wearer's skin, and capable of absorbing and retaining liquids such as urine and other certain body exudates. The absorbent core 147 may be manufactured in a wide variety of sizes and shapes (e.g., rectangular, hourglass, "T"-shaped, asymmetric, etc.) and from a wide variety of liquid-absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials. The configuration and construction of the absorbent core may also be varied (e.g., the absorbent core may have varying caliper zones, a hydrophilic gradient, a superabsorbent gradient, or lower average density and lower average basis weight acquisition zones; or may comprise one or more layers or structures). The total absorbent capacity of the absorbent core 147 should, however, be compatible with the design loading and the intended use of the diaper 144. Further, the size and absorbent capacity of the absorbent core 147 may be varied to accommodate wearers ranging from infants through adults. Exemplary absorbent structures for use as the absorbent core 147 are described in U.S. Pat. No. 4,610,678 entitled "High-Density Absorbent Structures"; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Weisman on Dec. 19, 1989; and U.S. Pat. No. 4,834,735, entitled "High Density Absorbent Members Having Lower Density and Lower Basis Weight Acquisition Zones", issued to Alemany et al. on May 30, 1989. Each of these patents are incorporated herein by reference.

The backsheet 146 is positioned adjacent the garment surface of the absorbent core 147 and is preferably joined thereto by attachment means (not shown) such as those well known in the art. For example, the backsheet 146 may be secured to the absorbent core 147 by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. and marketed as HL-1258. The attachment means will preferably comprise an open pattern network of filaments of adhesive as is disclosed in U.S. Pat. No. 4,573,986 entitled "Disposable Waste-Containment Garment", which issued to Minetola et al. on Mar. 4, 1986 more preferably several lines of adhesive filaments swirled into a spiral pattern such as is illustrated by the apparatus and methods shown in U.S. Pat. No. 3,911,173 issued to Sprague, Jr. On Oct. 7, 1975; U.S. Pat. No. 4,785,996 issued to Ziecker, et Al. on Nov. 22, 1978; and U.S. Pat. No. 4,842,666 issued to Werenicz on Jun. 27, 1989. Each of these Patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

The backsheet 146 is impervious to liquids (e.g., urine) and is preferably manufactured from a thin plastic film, although other flexible liquid impervious materials may also be used. As used herein, the term "flexible" refers to materials which are compliant and will readily conform to the general shape and contours of the human body. The backsheet 146 prevents the exudates absorbed and contained in the absorbent core 147 from wetting articles which contact the diaper 144 such as and undergarments. The backsheet 146 may thus comprise a woven or material, polymeric films such as thermoplastic films of polyethylene or polypropylene or, or composite materials such as a film-coated nonwoven material. Preferably, the backsheet is a film having a thickness of from about 0.012 mm (0.5 mil) to about 0.051 mm (2.0 mils). Particularly preferred materials for the backsheet include RR8220 blown films and RR5475 east films as manufactured by Tredegar Industries, Inc. of Terre Haute, Ind. The backsheet 146 is preferably embossed and/or matte finished to provide a more clothlike appearance. Further, the backsheet 146 may permit vapors to escape from the absorbent core 147 (i.e.breathable,) while still preventing exudates from passing through the backsheet 146.

The topsheet 145 is positioned adjacent the body surface of the absorbent core and is preferably joined thereto and to the backsheet 146 by attachment means (not shown) such as those well known in the art. Suitable attachment means are described with respect to joining the backsheet to the absorbent core 147. As used herein, the term "joined" encompasses configurations whereby an element is directly secured to the other element by affixing the element directly to the other element, and configurations whereby the element is indirectly secured to the other element by affixing the element to intermediate member(s) which in turn are affixed to the other element. In a preferred embodiment of the present invention, the topsheet 145 and the backsheet 146 are joined directly to each other in the diaper periphery 60 and are indirectly joined together by directly joining them to the absorbent core by the attachment means (not shown).

The topsheet 145 is compliant, soft feeling, and non-irritating to the wearer's skin. Further, the topsheet 145 is liquid pervious permitting liquids (e.g., urine) to readily penetrate through its thickness. A suitable topsheet may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene or fibers), or a combination of natural and synthetic fibers. Preferably, the topsheet 145 is made of a hydrophobic material to isolate the wearer's skin from liquids contained in the absorbent core 147. There are a number of manufacturing techniques which may be used to manufacture the topsheet 145. For example, the topsheet 145 may be a nonwoven web of fibers, spunbonded, carded, wet-laid, meltblown, hydroentagled, combinations of the above, or the like. A preferred topsheet is carded and thermally bonded by means well known to those skilled in the fabrics art. A preferred topsheet comprises a web of staple length polypropylene fibers such as is manufactured by Veratec, Inc., a Division of International Paper Company, of Walpole, Mass. under the designation P-8.

The diaper 144 preferably further comprises elasticized leg cuffs 153 for providing improved containment of liquids and other body exudates. Each elasticized leg cuff 153 may comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987, describes a disposable diaper having dual cuffs including a gasketing cuff and a barrier cuff.

The Diaper 144 preferably further comprises an elastic waist feature 154 that provides improved fit and containment. The elastic waist feature 154 is that portion or zone of the diaper 144 which is intended to expand and contract to dynamically fit the wearer's waist. The elastic waist feature 154 at least extends longitudinally outwardly from at least one of the waist edges of the absorbent core 147 and generally forms at least a portion of the end edge 155 of the diaper 144. Disposable diapers are generally constructed so as to have two elastic waist features, one positioned in the first waist region and one positioned in the second waist region, although diapers can be constructed with a single elastic waist feature. The elastic waist feature or any of its constituent elements can comprise a separate element affixed to the diaper 144, as shown in FIG. 17. Pre-stretched elastic spacing members 157, connected to an upper end of the waist features 154, cause the waist features 154 to stand up above the plane of the topsheet 145.

The elastic waist 154 may be constructed. in a number of different configurations including those described in U.S. Pat. No. 4,515,595 issued to Kievit et al. on May 7, 1985 and the above referenced U.S. patent application Ser. No 07/715, 152; each of these references being incorporated herein by reference.

The diaper 144 also comprises a fastening system which forms a side closure which maintains the first waist region 150 and the second waist region 152 in an overlapping configuration such that lateral tensions are maintained around the circumference of the diaper to maintain the diaper on the wearer. Exemplary fastening systems are disclosed in U.S. Pat. No. 4,846,815 entitled "Disposable Diaper Having An Improved Fastening Device" issued to Scripps on Jul. 11, 1989; U.S. Pat. No. 4,894,060 entitled "Disposable Diaper With Improved Hook Fastener Portion" issued to Nestegard on Jan. 16, 1990; U.S. Pat. No. 4,946, 527 entitled "Pressure-Sensitive Adhesive Fastener and Method of Making Same" issued to Battrell on Aug. 7, 1990; U.S. Pat. No. 3,848,594 entitled "Tape Fastening System for Disposable Diaper" issued to Buell on Nov. 19, 1974; U.S. Pat. No. B1 4,662,875 entitled "Absorbent Article" issued to Hirotsu et al. on May 5, 1987; and the hereinbefore referenced U.S. patent application Ser. No. 07/715,152; each of which is incorporated herein by reference.

In a preferred embodiment, the diaper also comprises elasticized side panels 158 disposed in the first waist region 150. (As used herein, the term "disposed" is used to mean that an element(s) of the diaper is formed (joined and positioned) in a particular place or position as a unitary structure with other elements of the diaper or as a separate element joined to another element of the diaper. The elasticized side panels 158 provide an elastically extensible feature that provides a more comfortable and contouring fit by initially conformably fining the diaper to the wearer and sustaining this fit throughout the time of wear well past when the diaper has been loaded with exudates since the elasticized side panels allow the sides of the diaper to expand and contract. The elasticized side panels 158 further provide more effective application of the diaper 144 since even if the diaper pulls one elasticized side panel farther than the other during application (asymmetrically), the diaper 144 will "self-adjust" during wear. While the diaper 144 of the present invention preferably has the elasticized side panels 158 disposed in the first waist region 150; alternatively, the diaper 144 may be provided with elasticized side panels 158 disposed in the second waist region 152 or in both the first waist region 150 and the second waist region 152. While the elasticized side panels 158 may be constructed in a number of configurations, examples of diapers with elasticized side panels positioned in the ears (ear flaps) of the diaper are disclosed in U.S. Pat. No. 4,857,067, entitled "Disposable Diaper Having Shirred Ears" issued to Wood, et al. on Aug. 15, 1989; U.S. Pat. No. 4,381,781 issued to Sciaraffa, et al. on May 3, 1983; U.S. Pat. No. 4,938,753 issued to Van Gompel, et al. on Jul. 3, 1990; and the hereinbefore referenced U.S. patent application Ser. No. 07/715,152; each of which are incorporated herein by reference.

FIG. 18 shows a frontal view of the apparatus 2 according to the invention and the applicator means 38 for applying a pre-stretched strip of elastic material, for instancek, laminate elastic material 161 to the web 1, such as for instance a waistband or a waistcap 154. The direction of transport of the web 1 is perpendicular to the plane of the drawing. The elastic material is 161 unwound from a roll by a metering element comprising two rolls 159, 160. Roll 159 is driven at slower speed than roll 160, so that the strip of elastic material is pre-stretched. The elastic material is fed along an automatic tracking system 162 to minimize cross-machine directional placement variations of the elastic material at the metering point that is located at the infeed point of the rotating perforated conveyor belt 165. A glue coater 164 intermittently coates the elastic material 161 with a continuous, or spiral-patterned layer of glue. The pre-stretched elastic material 161 is tightly held on the perforated conveyor belt 165 by action of vacuum suction box 166. The rotating conveyor belt 165 passes the elastic material under a crush knife 167, and subsequently rotates the elastic material in a parallel position to the web 1. The web 1 is stopped by the apparatus 2, and the air cylinders 29,29', as shown in FIG. 2, push the web 1 against the elastic element 161. Each air cylinder comprises a tamper foot. After a short dwell-time (a few milliseconds), the tamper feet of the air cylinders 29, 29' are moved upwards and the web 1 is accelerated in the direction of transport. Upon actuation of the air-cylinders 29,29', the vacuum acting on the prestretched elastic material 161 is switched off by means of a mechanical switch, blocking the access of the apertures in the conveyor 167 to the vacuum suction box 166. The movement of the transport rollers 13,15, the mechanical vacuum switch of the vacuum suction box 166, the air cylinders 29,29' the glue coater 164 and the crush knife 167 are all synchronised to maintain the proper phase relationship between the different movements.

FIG. 19a shows an embodiment in which the applicator means 38,38' comprise a pair of corrugated members 170, 171 having intermeshing teeth, for physically deforming the web 1. When the corrugated members 170, 171 are clamped down on the web 1, the web is deformed along parallel lines, corresponding to the corrugations which in this case extend perpendicular to the plane of drawing. The web has increased extensibility in the direction perpendicular to the lines of the deformations, the web 1 being after contacting with the corrugated members 170, 171 elongatable in a harmonica-like fashion. By stopping the web 1, relative to the corrugated members 170, 171, a complex pattern of deformation can be applied to the web which pattern for instance has a component in the transverse direction (cd-direction) of the web, so that the web is elongatable in the machine direction. By use of the apparatus according to the invention, it is possible to provide the leg portions 172 of the diaper, as is indicated in FIG. 20, with increased extensibility. Preferably, an elastic element is comprised between the topsheet and the backsheet in its relaxed state in the areas of deformation. Prior to contacting the web with the corrugated members 170, 171, the web 1 can not be substantially elongated, and can hence be transported without the need of a vacuum conveyor. After contacting the web with the corrugated members 170, 171, the areas of the web 1 in which the elastics are located are activated, and become elastically extensible.

The physical deformation can also be applied in the longitudinal direction of the web 1, for instance in the area of the side panels 158, or the waist areas, 173, 175 as shown in FIG. 20.

A known method for applying physical deformations to impart extensiblity to a web is commonly referred to as "ringrolling". Ringrolling involves passing the moving web between the nip of two rollers that are provided with circumferential corrugations. The axes of the rollers extend in the cross-machine direction of the web. Another form of "ringrolling" involves the use of flat corrugated members, of the type shown in FIGS. 19a and 19b of the present application. The above methods of ringrolling, as well as structures produced thereby have been described in detail in U.S. Pat. No. 5,196,000 issued to Clear et al. on Mar. 23, 1993; U.S. Pat. No. 5,167,897, issued to Weber et al. on Dec. 1, 1992; U.S. Pat. No. 5,156,793, issued to Buell et al. on Oct. 20, 1992, in particular FIG. 5, in combination with the description, Column 20; and U.S. Pat. No. 5,143,679, issued to Weber et al. on Sep. 1, 1992.

The method and apparatus according to the invention allow slow-speed deformation of the web 1. Hence the impact-times of the corrugated members on the web can be longer so that the physical deformation can be better dimensionally controlled and the energy imparted to the web can be more gradually distributed.

The apparatus according to the invention can be used to provide complex deformation patterns to products of the type described in the above patents. The physical deformation imparted by the method and apparatus according to the invention, can be so configured to impart extensibility to the whole of the absorbent product, such as the combined topsheet, backsheet and core, or to only portions thereof, such as to the lateral wings of a sanitary napkin as described in U.S. Pat. No. 4,687,478, issued to Van Tilburg on Aug. 18, 1987.

In FIG. 21, the web 1 is passed under an applicator 176 of absorbent gelling material, that is supplied to the applicator from a storage vessel 177. Applicators for dispensing particulate absorbent gelling material to a web, in particular powder spray guns, have been described in U.S. Pat. No. 4,543,274, issued to Mulder et al. on Sep. 24, 1985 and European Patent EP-B-0 330 675. By accelerating the web 1 with respect to the applicator 176, the concentration of absorbent gelling material in the core can be varied in the machine direction, at a constant rate of deposition by the applicator.

I claim:

1. Method of making an absorbent article (144), the article comprising a liquid-pervious topsheet (121, 145), a liquid impervious backsheet (123, 146) and an absorbent core (120, 147) interposed between the topsheet and the backsheet, the method comprising the steps of:

a) feeding a web (1), comprising the topsheet (121, 145) the backsheet (123, 146) or the core (120, 147) or a combination thereof along a stationary frame (35), along an upstream trajectory (3), a downstream trajectory (5), and an intermediate trajectory (7a, 7b, 7c) comprised between the upstream trajectory and the downstream trajectory, the web (1) having along the upstream trajectory (3) and along the downstream trajectory (5) a substantially constant speed of transport, the upstream and the downstream trajectory (3, 5) being substantially stationary relative to the frame (35), b) running the web (1) along an upstream and a downstream guide roller (9, 11) that are translationally stationary relative to the frame (35) and along an upstream and a downstream transport roller (13, 15) that are periodically displaced, said upstream and downstream transport rollers (13, 15) are connected to a displacement balancing means (77), the transport rollers and the displacement balancing means being reciprocated, a combined center of mass of the displacement balancing means and the transport roller being maintained in a stationary position such that:

a first section (7a) of the intermediate trajectory (7a, 7b, 7c) of the web (1) extends between the upstream guide roller (9) and the upstream transport roller (13), a second section (7b) of the intermediate trajectory (7a, 7b, 7c) extends between the upstream guide roller (9) and the downstream guide roller (11) or between the upstream transport roller (13) and the downstream transport roller (15), and a third section 7c of the intermediate trajectory (7a, 7b, 7c) extends between the downstream guide roller (11) and the downstream transport roller (15), the first section (7a) and the third section (7c) of the intermediate trajectory (7a, 7b, 7c) of the web, (1) being parallel to the second section (7b) of the intermediate trajectory, c) periodically displacing the transport rollers (13, 15) relative to the guide rollers (9, 11) around a stationary equilibrium position (39) in a direction substantially parallel to the second section (7b) of the intermediate trajectory of the web (1), while keeping constant a length of the intermediate trajectory (7a, 7b, 7c) and while keeping constant a length of the second section (7b) of the intermediate trajectory and d) rotating the transport rollers (13, 15) such that strain exerted on the web (1) in running the web past the transport rollers (13, 15) is not substantially larger than strain exerted on the web by inertia forces acting on the web (1).

2. Method according to claim 1, wherein the guide rollers (9,11) are rotated.

3. Method according to claim 1, the guide rollers (9,11) and the transport rollers (12,15) being driven by a drive member (50) which is coupled with the guide rollers and the transport rollers to form a closed loop, a part of which extends parallel to the intermediate trajectory (7a, 7b, 7c), the drive member (50) being driven at a constant speed.

4. Method according to claim 1, the transport rollers (13,15) being connected to a rotation-balancing means (63, 63'), such that variations in torque exerted by the transport rollers (13,15) are reduced.

5. Method according to claim 4, the method further comprising driving the transport rollers (13,15) and the rotation-balancing means (63, 63') in combination, at constant torque.

6. Method of making an absorbent article (144), the article comprising a liquid-pervious topsheet (121, 145), a liquid impervious backsheet (123, 146) and an absorbent core (120, 147) interposed between the topsheet and the backsheet, the method comprising the steps of:

a) feeding a web (1), comprising the topsheet (121, 145) the backsheet (123, 146) or the core (120, 147) or a combination thereof along a stationary frame (35), along an upstream trajectory (3), a downstream trajectory (5), and an intermediate trajectory (7a, 7b, 7c) comprised between the upstream trajectory and the downstream trajectory, the web (1) having along the upstream trajectory (3) and along the downstream trajectory (5) a substantially constant speed of transport, the upstream and the downstream trajectory (3, 5) being substantially stationary relative to the frame (35), b) running the web (1) along an upstream and a downstream guide roller (9, 11) that are translationally stationary relative to the frame (35) and along an upstream and a downstream transport roller (13, 15), wherein the periodically displaceable transport rollers (13, 15) are connected to a displacement balancing means (77), such that:

a first section (7b) of the intermediate trajectory (7a, 7b, 7c) of the web (1) extends between the upstream guide roller (9) and the upstream transport roller (13), a second section (7b) of the intermediate trajectory (7a, 7b, 7c) extends between the upstream guide roller (9) and the downstream guide roller (11) or between the upstream transport roller (13) and the downstream transport roller (15), and a third section (7c) of the intermediate trajectory (7a, 7b, 7c) extends between the downstream guide roller (11) and the downstream transport roller (13), the first section (7a) and the third section (7c) of the intermediate trajectory (7a, 7b, 7c) of the web, (1) being parallel to the second section (7b) of the intermediate trajectory, c) periodically displacing the transport rollers (13, 15) relative to the guide rollers (9,11) around a stationary equilibrium position (39) at a frequency of between 1 Hz and 100 Hz, in a direction substantially parallel to the second section (7b) of the intermediate trajectory (7a, 7b, 7c) of the web (1), while keeping constant the length of the intermediate trajectory (7a, 7b, 7c) and while keeping constant the length of the second section (7b) of the intermediate trajectory, and d) moving the displacement-balancing means (77) so as to keep a combined center of mass of the transport rollers (13, 15) and the displacement balancing means (77) substantially stationary.

7. Method according to claims 1 or 6, wherein the periodic speed at which the transport rollers (13, 15) are moved relative to the guide rollers (9, 11) has an amplitude of 1/(2n) times a speed of transport, so that the second section (7b) of the intermediate trajectory (7a, 7b, 7c) is periodically stationary with respect to the frame (35), wherein n is a natural member.

8. Method according to claims 1 or 6, the method including, for a part of the web that is located along the second section (7b) of the intermediate trajectory (7a, 7b, 7c), any of the following steps or combinations thereof:

applying an adhesive to the web, applying a tape fastening system to the web, applying an absorbent gelling material to the web, applying a waist feature to the web, applying a reinforcement strip to the web or imparting an increased extensibility to the web.

9. Apparatus (2) for manufacturing an absorbent article (144), the article comprising a liquid-pervious topsheet (121, 145), a liquid impervious backsheet (123, 146) and an absorbent core (120, 147) interposed between the topsheet and the backsheet, the apparatus comprising:

a stationary frame (35), an upstream and a downstream guide roller (9, 11) connected to the frame (35) in a translationally stationary manner, each guide roller (9, 11) having an axis (19, 21), the axes (19, 21) being generally parallel, the guide rollers (9, 11) being rotatable around their axes (19, 21), the rotational drive means (50, 51) a drive member (50) which is run along guide rollers (9, 11) and the transport rollers (13, 15) to form a closed loop, and a drive motor (51) driving the drive member (50) at a constant speed and a constant direction of rotation, and upstream and a downstream rotatable, cylindrical transport roller (13, 15), the axes (25, 27) of which are generally parallel to the axes (19, 21) of the guide rollers (9, 11), the cylindrical surface of the upstream guide roller (9) and the upstream transport (134) roller being substantially tangent to a first plane (29), the cylindrical surface of the downstream guide roller (11) and the downstream transport roller (15) being substantially tangent to a second plane (31) which is substantially parallel the first plane (29), and a circumferential surface of both guide rollers (9, 11) or both transport rollers (13, 15) being substantially tangent to a third plane (33) which is located at a spaced apart location from the first plane (29) and the second plane (31) and which is parallel thereto, translational drive means (36, 71) connected to the frame (35) for periodically displacing the transport rollers (13, 15) generally perpendicular to the axes (25, 27) of the transport rollers (13, 15), around an equilibrium position (39) located generally midway between the axes (19, 21) of the guide rollers (9, 11), a distance between the axes (25, 27) of the transport rollers being constant, rotational drive means (50, 51) for rotating the transport rollers (13, 15) in synchronism with the displacement of the transport rollers, such that when a web (1) comprising the topsheet, the backsheet, the core or any combination thereof, is run past the transport members (13, 15), strain on the web (11) is not substantially larger than strain exerted on the web by inertia forces acting on the web (1), and rotation balancing means (63, 63') for each transport roller (13, 15) a rotatable disc (65, 65')a phase of the rotational speed of which differs by 180°, or a whole multiple thereof from the phase of the rational speed of the transport rollers (13, 15), so that the transport rollers (13, 15) and the balancing means (63, 63') in combination can be rotated at a constant torque.

10. Apparatus according to claim 9, the transport rollers (13,15) being connected to a sled (41) which is mounted on the frame (35) so as to be movable relative to the frame (35).

11. Apparatus according to claim 10, the rotation-balancing means (63, 63') comprising for each transport roller (13, 15):

two pulleys (67, 67', 69, 69') connected to a sled (41), one pulley (67, 67') being driven by a respective transport roller (13, 15) and a belt (70, 70') fed around the circumference of a disc (65, 65') and around both respective pulleys (67, 69, 67', 69') to form a closed loop.

12. Apparatus according to claim 11, the transport rollers (13, 15) being connected to a translation-balancing means (77) to maintain a generally constant position of a combined center of mass of the balancing means (77), the transport rollers (13, 15) and the sled (41).

13. Apparatus (2) for manufacturing an absorbent article (144), the article comprising a liquid-pervious topsheet (121, 145), a liquid impervious backsheet (123, 146) and an absorbent core (129, 147) interposed between the topsheet (121, 145) and the backsheet (123, 146), the apparatus comprising:

a stationary frame (35), an upstream and a downstream guide roller (9, 11) which are connected to the frame (35) in a translationally stationary manner, each guide roller (9, 11) having an axis (19, 21), the axes (19, 21) being generally parallel, an upstream and a downstream, rotatable, cylindrical transport roller (13, 15), the guide rollers being connected to a sled (41) which is translationally mounted on the frame (35) the axes (25, 27) of which are generally parallel to the axes (19, 21) of the guide rollers (9, 11), the cylindrical surface of the upstream guide roller (9) and the upstream transport roller (13) being substantially tangent to a first plane (29), the cylindrical surface of the downstream guide roller (11) and the downstream transport roller (15) being substantially tangent to a second plane (31) which is substantially parallel to the first plane, and a circumferential surface of both guide rollers (9, 11) or both transport rollers (13, 15) being substantially tangent to a third plane (33) which is located at a spaced apart location from the first plane (29) and the second plane (31) and which is parallel thereto, translational drive means (36, 71) connected to the sled (41) for periodically displacing the transport rollers (13, 15) generally perpendicular to the axes (25, 27) of the transport rollers, around an equilibrium position (39) located generally midway between the axes (19, 21) of the guide rollers (9, 11), the distance between the axes (25, 27) of the transport rollers (13, 15) being constant, and translation-balancing means (77) to maintain a generally constant position of a center of mass of the balancing means (77), the transport rollers (13, 15) and the sled (41).

14. Apparatus (2) according to claims 9 or 13, wherein the first and the second plane (29,31) are coincident, a distance between the axes (25,27) of the transport rollers (13,15) being larger than a distance between the axes (19,21) of the guide rollers (9,11) and wherein the transport rollers (13,15) are displaceable in a substantially straight line.

15. Apparatus according to claim 14, a distance between the axes (25,27) of the transport rollers being (13,15) smaller than a distance between the axes (19,21) of the guide rollers, (9,11) and wherein the transport rollers. (13,15) are displace along a circular path.

16. Apparatus according to claims 9 or 13, the sled (41) being suspended from the frame (35) by a suspension means (79,79') comprising two vertical arms (89,89'), a lower end (96,96') of each arm (79,79') being connected to a respective end of the sled (41), each vertical arm (89,89') being at its upper end hingably connected to the frame (35).

17. Apparatus according to claim 16, the upper end of each vertical arm (89,89') of the suspension means (79,79') being connected in a hinging point (108) to a first side of a transverse arm (93,93'), the transverse arm (93,93')being at a second side hingingly connected to the frame (35), each vertical arm (89,89') being hingably connected at its midpoint (97,97') to an upper end of a further vertical arm (86,86') that extends generally parallel to the vertical arm (89,89') and has a length of generally half of the length of the vertical arm (89, 89'), a lower end of the further vertical arm (86, 86') being hingably connected to the frame (35).

18. Apparatus according to claims 9 or 13, the translational drive means (36, 71) comprising a reciprocatable cantilever (71), connected to the frame (35) in a pivot point (75), the cantilever (71) being connected to the sled (41) in a drive point (73).

19. Apparatus according to claim 18, a distance between the pivot point (75) and the drive point (73) being adjustable.

20. Apparatus according to claims 9 or 13, the apparatus including applicator means (38,38') which are positionally stationary relative to the frame (35), the applicator means (38, 38') including any of the following or combinations thereof:

an glue applicator for applying an adhesive to a web (1), gripper means, in particular a vacuum gripper, for applying a tape fastening system, a waist feature or a reinforcement strip to a web (1), dispensing means (176) for applying an absorbent gelling material to a web (1), or corrugated deformation members (170, 171) for imparting an increased extensibility to a web (1) or a part thereof.

* * * * *

UNITED STATES PATENT AND TRADEMARK OFFICE
CERTIFICATE OF CORRECTION

PATENT NO. : 5,693,165            Page 1 of 1
DATED : December 2, 1997
INVENTOR(S) : Christoph Schmitz et al.

It is certified that error appears in the above-identified patent and that said Letters Patent is hereby corrected as shown below:

Column 23,
Line 61, "member" should read -- number --.

Signed and Sealed this

Eighth Day of January, 2002

Attest:

JAMES E. ROGAN
Attesting Officer      Director of the United States Patent and Trademark Office